US008362071B2

(12) United States Patent
Chen et al.

(10) Patent No.: US 8,362,071 B2
(45) Date of Patent: *Jan. 29, 2013

(54) ANTIADHESION AGENTS

(75) Inventors: Ching-Shih Chen, Upper Arlington, OH (US); Dasheng Wang, Dublin, OH (US); Samuel K. Kulp, Hilliard, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 300 days.

This patent is subject to a terminal disclaimer.

(21) Appl. No.: 12/761,504

(22) Filed: Apr. 16, 2010

(65) Prior Publication Data

US 2010/0267820 A1 Oct. 21, 2010

Related U.S. Application Data

(60) Provisional application No. 61/170,316, filed on Apr. 17, 2009.

(51) Int. Cl.
*A61K 31/355* (2006.01)
*C07D 311/00* (2006.01)
(52) U.S. Cl. ........................ 514/458; 549/408
(58) Field of Classification Search .................. 514/458; 549/408
See application file for complete search history.

(56) References Cited

U.S. PATENT DOCUMENTS

| | | | |
|---|---|---|---|
| 2,680,749 | A | 6/1954 | Cawley et al. |
| 4,262,017 | A | 4/1981 | Kuipers et al. |
| 6,004,565 | A | 12/1999 | Chiba et al. |
| 6,121,329 | A | 9/2000 | Fujii et al. |
| 6,417,223 | B1 | 7/2002 | Sanders et al. |
| 6,476,004 | B1 | 11/2002 | Sakai et al. |
| 6,645,998 | B2 | 11/2003 | Sanders et al. |
| 6,703,384 | B2 | 3/2004 | Sanders et al. |
| 6,770,672 | B1 | 8/2004 | Sanders et al. |
| 6,858,227 | B1 | 2/2005 | Lal et al. |
| 2004/0235938 | A1 | 11/2004 | Sanders et al. |
| 2004/0248971 | A1 | 12/2004 | Yeh et al. |
| 2005/0065149 | A1 | 3/2005 | Wang et al. |
| 2005/0090520 | A1 | 4/2005 | Lindquist |
| 2005/0215531 | A1 | 9/2005 | Baumruker et al. |
| 2008/0009545 | A1 | 1/2008 | Chen et al. |
| 2008/0161349 | A1 | 7/2008 | Sanders et al. |
| 2009/0137530 | A1 | 5/2009 | Kiuchi et al. |
| 2010/0022655 | A1 | 1/2010 | Byrd et al. |
| 2010/0179216 | A1 | 7/2010 | Kiuchi et al. |
| 2010/0267673 | A1 | 10/2010 | Chen et al. |
| 2010/0273871 | A1 | 10/2010 | Chen et al. |

FOREIGN PATENT DOCUMENTS

| | | |
|---|---|---|
| JP | 59-222415 | 12/1984 |
| WO | 03/039461 | 5/2003 |
| WO | 01/588889 | 8/2006 |
| WO | 2007/098139 | 8/2007 |
| WO | 2007/143081 | 12/2007 |
| WO | 2008/021532 | 2/2008 |
| WO | 2010/042998 | 4/2010 |
| WO | 2010/120711 | 10/2010 |
| WO | 2010/121111 | 10/2010 |

OTHER PUBLICATIONS

Calabresi P and Chabner BA, "Section IX Chemotherapy of Neoplastic Diseases—Introduction," Goodman & Gilman's The Pharmacological Basis of Therapeutics 10th ed., 2001, Hardman JG, Limbird LE, and Gilman AG, Eds, McGraw-Hill, New York 2001, 1381-1388 (pp. 1381, 1383-1385, and 1388 provided).*
International Search Report and Written Opinion from PCT/US07104337 dated Sep. 19, 2008.
International Search Report and Written Opinion from PCT/US10/30799 dated May 18, 2010.
Interview Summary from U.S. Appl. No. 11/708,792 dated Apr. 9, 2009.
Office action from U.S. Appl. No. 11/708,792 dated Jul. 6, 2009.
Response to Office action from U.S. Appl. No. 11/708,792 dated Aug. 12, 2009.
Office action from U.S. Appl. No. 11/708,792 dated Nov. 27, 2009.
Communication from European Application No. 07751119.4 dated Mar. 13, 2009.
Arya P., et al., "Design and Synthesis of Analogs of Vitamin E: Antiproliferative Activity Against Human Breast Andenocarcinoma Cells", Bioorganic & Medicinal Chemistry Letters, vol. 8, 1998, pp. 2433-2438.
Bang et al., "Activation of PKC but not of ERK is required for vitamin E-succinate-induced apoptosis of HL-60 cells", Biochem Biophys Res. Commun, 288, pp. 789-97 (2001).
Barnett et al., "Vitamin E succinate inhibits colon cancer liver metastases", J Surg Res 106, pp. 292-298 (2002).
Roberts et al., "Antitumor activity and pharmacology of a selective focal adhesion kinase inhibitor, PF-562,271", Cancer Res 68, pp. 1935-1944 (2008).
Birringer et al., "Vitamin E analogues as inducers of apoptosis: structure-function relation", Br J Cancer 88, pp. 1948-1955 (2003).

(Continued)

*Primary Examiner* — Paul Zarek
(74) *Attorney, Agent, or Firm* — Tarolli, Sundheim, Covell & Tummino LLP

(57) ABSTRACT

Vitamin E succinate derivatives according to formula I:

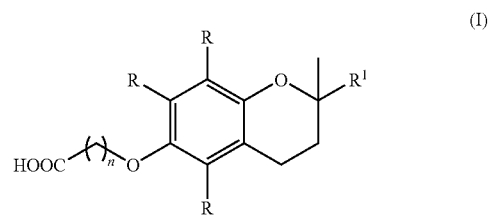

are described. These compounds can be included in pharmaceutical compositions, and can be used for the treatment of cancers such as metastatic cancer and as antiadhesive agents.

13 Claims, 6 Drawing Sheets

OTHER PUBLICATIONS

Chen et al., "Molecular determinants of resistance to antiandrogen therapy," Nat. Med 10, pp. 33-39 (2004).

Qian et al., "c-Jun involvement in vitamin E succinate induced apoptosis of reticuloendotheliosis virus transformed avian lymphoid cells", Oncogene 15, pp. 223-230 (1997).

Prasad et al., "a-Tocopheryl succinate, the most effective form of vitamin E for adjuvant cancer treatment: A review", J Am Coll Nutr 22, pp. 108-117 (2003).

Chuang et al., "Phosphorylation by c-Jun NH2-terminal kinase 1 regulates the stability of transcription factor Sp1 during mitosis", Mol Biol Cell 19, pp. 1139-1151 (2008).

Crispen et al., "Vitamin E succinate inhibits NF-kappaB and prevents the development of a metastatic phenotype in prostate cancer cells: implications for chemoprevention", Prostate, 67, pp. 582-90 (2007).

Degterev et al., "Identification of small-molecule inhibitors of interaction between the BH3 domain and Bcl-x", Nat. Cell Biol, 3, pp. 173-182 (2001).

Dong et al., "Vitamin E analogues inhibit angiogenesis by selective induction of apoptosis in proliferating endothelial cells: the role of oxidative stress", Cancer Res 67, pp. 11906-11913 (2007).

Gu et al., "Vitamin E succinate induces ceramide-mediated apoptosis in head and neck squamous cell carcinoma in vitro and in vivo", Clin Cancer Res, 14, pp. 1840-1848 (2008).

Hahn et al., "Dietary administration of the proapoptotic vitamin E analogue alpha-tocopheryloxyacetic acid inhibits metastatic murine breast cancer", Cancer Res 66, pp. 9374-9378 (2006).

Huang et al., "a-Tocopheryl succinate and derivatives mediate the transcriptional repression of androgen receptor in prostate cancer cells by targeting the PP2A-JNK-Sp1 Signaling axis", Carcinogenesis, vol. 30, No. 7, pp. 1125-1131, 2009.

Janssens et al., "Protein phosphatase 2A: a highly regulated family of serine/threonine phosphatases implicated in cell growth and signalling", Biochem J, 353, pp. 417-439 (2001).

Juntilla et al., "CIP2A inhibits PP2A in human malignancies", Cell, 130, pp. 51-62 (2007).

Kogure et al., "Potentiation of anti-cancer effect by intravenous administration of vesiculated tocophyeryl hemisuccinate on mouse melanoma in vivo", Cancer Lett, 192, pp. 19-24 (2003).

Lawson et al., "Novel vitamin E analogue decreases syngeneic mouse mammary tumor burden and reduces lung metastasis", Mol Cancer Ther, 2, pp. 437-444 (2003).

Lei et al., "The Bax subfamily of Bcl2-related proteins is essential for apoptotic signal transduction by c-Jun NH(2)-terminal kinase", Mol Cell Biol, 22, pp. 4929-4942 (2002).

Lockwood et al., "Anti-adhesion molecule therapy as an interventional strategy for autoimmune inflammation", Clin Immunol, 93, pp. 93-106 (1999).

Lugovskoy et al., "A Novel approach for characterizing protein ligand complexes: Molecular basis for specificity of small-molecule Bcl-2 inhibitors", J Am Chem Soc, 124, pp. 1234-1240 (2002).

Malafa et al., "Vitamin E succinate promotes breast cancer tumor dormancy", J Surg Res, 93, pp. 163-170 (2000).

Malafa et al., "Inhibition of angiogenesis and promotion of melanoma dormancy by vitamin E succinate", Ann Surg Oncol 9, pp. 1023-1032 (2002).

McLean et al., "The role of focal-adhesion kinase in cancer—a new therapeutic opportunity", Nat Rev Cancer 5, pp. 505-515 (2005).

Mitra et al., "Integrin-regulated FAK-Src signaling in normal and cancer cells", Curr Opin Cell Biol 18, pp. 516-523 (2006).

Mitra et al., "Focal adhesion kinase: in command and control of cell motility", Nat Rev Mol Cell Biol, 6, pp. 56-68 (2005).

Neuzil et al., "Induction of cancer cell apoptosis by alpha-tocopheryl succinate: molecular pathways and structural requirements", FASEB J, 15, pp. 403-415 (2001).

Neuzil et al., "Selective cancer cell killing by tocopheryl succinate", Br. J. Cancer, 84, pp. 87-89 (2001).

Neuzil et al., "a-Tocopheryl succinate epitomizes a compound with a shift in biological activity due to pro-vitamin-to-vitamin conversion", Biochem Biophys Res Commun, 293, pp. 1309-1313 (2002).

Neuzil et al., "Vitamin E analogs, a novel group of "mitocans," as anticancer agents: the importance of being redox-silent", Mol Pharmacol, 71: pp. 1185-1199 (2007).

Ni et al., "Vitamin E succinate inhibits human prostate cancer cell growth via modulating cell cycle regulatory machinery", Biochem Biophys Res Commun, 300, pp. 357-363 (2003).

Prasad et al., "Effects of tocopherol (Vitamin E) acid succinate on morphological alterations and growth inhibition in melanoma cells in culture", Cancer Res 42, pp. 550-555 (1982).

Schmidmaier et al., Curr Med Chem 15, pp. 978-990 (2008).

Shanker et al., "Vitamin E succinate in combination with mda-7 results in enhanced human ovarian tumor cell killing through modulation of extrinsic and intrinsic apoptotic pathways", Cancer Lett, 254, pp. 217-226 (2007).

Shiau et al., "a-tocopheryl succinate induces apoptosis in prostate cancer cells in part through inhibition of Bcl-xL/Bcl-2 function", J Biol Chem, 281, pp. 11819-11825 (2006).

Simmons et al., "Anti-adhesion therapies", Curr Opin Pharmacol, 5, pp. 398-404, (2005).

Van Assche et al., "Physiological basis for novel drug therapies used to treat the inflammatory bowel diseases. I. Immunology and therapeutic potential of antiadhesion molecule therapy in inflammatory bowel disease", Am J Physiol Gastrointest Liver Physiol, 288, pp. G169-G174 (2005).

Wang et al., "Vitamin E analogues as anticancer agents: lessons from studies with alpha-tocopheryl succinate", Mol. Nutr. Food Res., 50, pp. 675-685 (2006).

Wang et al., "A peptide conjugate of vitamin E succinate target breast cancer cells with high ErbB2 expression", Cancer Res 67, pp. 3337-3344 (2007).

Wang et al., "a-Tocopheryl succinate as a scaffold to develop potent inhibitors of breast cancer cell adhesion", J Med Chem 52, pp. 5642-5648 (2009).

Weber et al., "Vitamin E succinate is a potent novel antineoplastic agent with high selectivity and cooperativity with tumor necrosis factor-related apoptosis-inducing ligang (Apo2 ligand) in vivo", Clin Cancer Res 8, pp. 863-869 (2002).

Weber et al., "Mitochondria play a central role in apoptosis induced by alpha-tocopheryl succinate, an agent with antineoplastic activity: comparison with receptor-mediated pro-apoptotic signaling", Biochemistry, 42, pp. 4277-4291 (2003).

Wu et al., "Cellular and molecular effects of alpha-tocopheryloxybutyrate: Lessions for the design of vitamin E analog for cancer prevention", Anticander Research, Helenic Anticancer Institute, Athens, vol. 24, No. 6, Nov. 1, 2004 pp. 3795-3802.

Yin et al., "The therapeutic and preventive effect of RRR-alpha-vitamin E succinate on prostate cancer via induction of insulin-like growth factor binding protein-3", Clin Cancer Res, 13, pp. 2271-2280 (2007).

You et al., "RRR-alpha-tocopheryl succinate induces MDA-MB-435 and MCF-7 human breast cancer cells to undergo differentiation", Cell Growth Differ, 12, pp. 471-480 (2001).

You et al., "Role of extracellular signal-regulated kinase pathway in RRR-alpha-tocopheryl succinate-induced differentiation of human MDA-MB-435 breat cancer cells", Mol Carcinog, 33, pp. 228-236 (2002).

Yu et al., "Activation of extracellular signal-regulated kinase and c-Jun-NH(2)-terminal kinase but not p38 mitogen-activiated protein kinases is required for RRR-alpha-tocopheryl succinate-induced apoptosis of human breast cancer cells", Cancer Res 61, pp. 6569-6576 (2001).

Zhang et al., "Vitamin E succinate inhibits the function of androgen receptor and the expression of prostate-specific antigen in prostate cancer cells", Proc Natl Acad Sci USA, 99, pp. 7408-7413 (2002).

Zhao et al., "alpha-tocopheryl succinate-induced apoptosis in human gastric cancer cells is modulated by ERK1/2 and c-Jun N-terminal kinase in a biphasic manner", Cancer Lett, 247, pp. 345-352 (2007).

Tchou et al., "GSTP1 CpG island DNA hypermethylation in hepatocellular carcinomas", Int J Onjcol, 16, pp. 663-676 (2000).

Tedesco-Silva et al., "FTY720, a novel immunomodulator: efficacy and safety results from the first phase 2A study in de novo renal transplantation. Transplantation, 77: 1826-1833, 2004."

Tedesco-Silva et al., FTY720, a novel immunomodulator: efficacy and safety results from the first phase 2A study in de novo renal transplantation. Transplantation, 79: 1553-1560, 2005.
Thomas, et al., "Drug-induced apoptosis in B-cell chronic lymphocytic leukemia: relationship between p53 gene mutation and bcl-2/bax proteins in drug resistance", Oncogene 12: pp. 1055-1062 (1996).
Thomas, et al., "Opportunities for Targeted Therapies in Hepatocellular carcinoma", J. Clin Oncol. 23, pp. 8093-8108 (2005).
Tseng et al., "Overcoming trastuzumab resistance in HER2-overexpressing breast cancer cells by using a novel celecoxib-derived phosphoinositide-dependent kinase-1 inhibitor", Mol Pharmacol 70, pp. 1534-1541 (2006).
Varga et al., "Tumor grade-depdneent alterations in the protein kinase C isoform pattern in urinary bladder carcinomas", Eur Urol 46, pp. 462-465 (2004).
Weber et al., "Induction of cancer cell apoptosis by alpha-tocopheryl succinate: molecular pathways and structural requirements", FASEB, J., 15 (2) Feb. 2001.
Yasui et al., "FTY720 induces apoptosis in multiple myeloma cells and overcomes drug resistance", Cancer Research, 65: 7478-7484 (2005).
Yusof et al., "Immunohistochemical expression of π class glutathione S-transferase and α-Fetoprotein in hepatocellular carcinoma and chronic liver disease", Anal Quant Cytol Histol, 25, pp. 332-338 (2003).
Zhou et al., "FTY720, a fungus metabolite, inhibits invasion ability of androgen-independent prostate cancer cells through inactivation of RhoA-GTPase", Cancer Letters, 233: 36-47 (2006).
Ho et al., "Effects of a novel immunomodulating agent, FTY720, on tumor growth and angiogenesis in hepatocellular carcinoma", Molecular Cancer Therapeutics, 4: 1430-1438 (2005).
Hoshino et al., "FTY720, a novel immunosuppressant possessing unique mechanims. II. Long-term graft survival induction in rat heterotopic cardiace allografts and synergistic effect in combination with cyclosporine A", Transplantation Proceedings, 28: pp. 1060-1061 (1996).
Hung et al., FTY720 induces apoptosis in hepatocellular carcinoma cells through activation of protein kinase Cδ signaling, Cancer Res 68, pp. 1204-1212 (2008).
Jackson et al., "The enigmatic protein kinase Cδ: complex roles in cell proliferation and survival", FASEB J, 18, pp. 627-636 (2004).
Johnson et al., "A novel celecoxib derivative, OSU03012, induces cytotoxicity in primary CLL cells and transformed B-cell lymphoma cell line via a caspase- and Bcl-2-independent mechanism", Blood, v.105, p. 2504-2509 (2005).
Kahan et al., "Pharmacodynamics, pharmacokinetics, and safety of multiple doses of FTY720 in stable renal transplant patients: a multicenter, randomized, placebo-controlled, phase I study. Transplantation, 76: 1079-1084, 2003".
Kawaguchi et al., "FTY720, a novel immunosuppressant possessing unique mechanisms. III. Synergistic prolongation of canine renal allograft survival in combination with cyclosporine A", Transplantation Proceedings 28: pp. 1062-1063 (1996).
Kitada et al. "Expression of apoptosis-regulating proteins in chronic lymphocytic leukemia: correlations with in vitro and in vivo chemoresponses", Blood, 91: 3379-3389 (1998).
Kiuchi et al., "Synthesis and immunosuppressive activity of 2-substituted 2-aminopropane-1, d-diols and 2-aminoethanols", J Med Chem 43, pp. 2946-2961 (2000).
Koopman et al., Annexin V for flow cytometric detection of phosphatidylserine expression on B cells undergoing apoptosis. Blood, 84: 1415-1420, 1994.
Lee et al., "FTY720 induces apoptosis of human hepatoma cell lines through PI3-K-mediated Akt dephosphorylation", Carcinogenesis, 25: 2397-2405 (2004).
Lee et al., "Significance of the Rac signaling pathway in HCC cell motility: implications for a new therapeutic target", Carcinogenesis, 26: 681-687 (2005).
Lee et al., "FTY720: a promising agent for treatment of metastatic hepatocellular carcinoma. Clinical Cancer Research : an Official Journal of the American Association for Cancer Research", 11: 8458-8466 (2005).
Li et al., "The myeloid leukemia-associated protein SET is a potent inhibitor of protein phosphatase 2A", J. Biol. Chem. 271, pp. 11059-11062 (1996).
Li et al., "Induction of lymphocyte apoptosis by a novel immunosuppressant FTY720: relation with Fas, Bcl-2 and Bax expression", Transplantation Proceedings, 29: 1267-1268 (1997).
Li Dengju et al., "Role of extracellular regulated protein kinases in FTY720-induced apoptosis of leukemia cell lines HL-60 and U937", Journal of Huazhong University of Science and Technology [Med Sci], 24, p. 45-47 (2004).
Liu, "Small molecule antagonists of LFA-1/ICAM-1 interactions as potential therapeutic agents", Expert Opinion Ther. Patents, 11 (9): pp. 1383-1393 (2001).
Llovet et al., "Sorafenib in advanced hepatocellular carcinoma", N Engl J Med, 359, pp. 378-390 (2008).
Martin, R., "Closing in on an oral treatment" Multiple Sclerosis, Nature 464, pp. 360-362 (2010).
Masubuchi et al., "FTY720, a novel immunosuppressant, possessing unique mechanisms. IV. Prevention of graft versus host reactions in rats. Transplantation Proceedings, 28: 1064-1065, 1996".
Matsuoka et al., "Reduction of phosphorylated Akt/PKB by immunosuppressant FTY720" Cell Biology International, 24, p. 976-977 (2000).
Matsuoka et al, "A novel immunosuppressive agent FTY720 induced Akt dephosphorylation in leukemia cells", British Journal of Pharmacology, 138: 1303-1312 (2003).
McConkey, et al., "Apoptosis sensitivity in chronic lymphocytic leukemia is detrmined by endogenous endonuclease content and relative expression of BCL-2 and BAX", J. Immunol. 156: pp. 2624-2630 (1996).
Moon et al., "PDE4 inhibitors activate a mitochondrial apoptotic pathway in chronic lymphocytic leukemia cells that is regulated by protein phosphatase 2A", Blood 101, pp. 4122-4130 (2003).
Morley et al., "Proteasome inhibitors and immunosuppressive drugs promote the cleavage of eIF4GI and eIF4GII by caspase-8-independent mechanisms in Jurkat T cell lines" FEBS Letters, 503: 206-212 (2001).
Mullershausen et al., "Persistent signaling induced by FTY720-phosphate is mediated by internalized S1P1 receptors", Nat Chem Biol 5, pp. 428-434 (2009).
Nagahara et al., "Evidence that FTY720 induces T cell apoptosis in vivo", Immunopharmacology, 48: 75-85 (2000).
Nagahara et al., "Immunosuppressant FTY720 induces apoptosis by direct induction of permeability transition and release of cytochrome c from mitochondria", Journal of Immunology, 165, p. 3250-3259 (2000).
Nagahara et al., "Coordinate involvement of cell cycle arrest and apoptosis strengthen the effect of FTY720", Japanese Journal of Cancer Research : 92: 680-687 (2001).
Nagahara et al., "T cell selective apoptosis by a novel immunosuppressant, FTY720, is closely regulated with Bcl-2", British Journal of Pharmacology, 137: 953-962 (2002).
Omar et al., "Targeting of the Akt-nuclear factor-κB signaling network by [1-(4-chloro-3-nitrobenzenesulfonyl)-1H-indol-3-yl]-methanol (OSU-A9), a novel indole-3-carbinol derivative, in a mouse model of hepatocellular carcinoma", Mol Pharmacol 76, pp. 957-968 (2009).
Pabst et al., "Enhanced FTY720-mediated lymphocyte homing requires G alpha i signaling and depends on beta 2 and beta 7 integrin", J. Immunol, 176: 1474-1480 (2006).
Prieschl, "The balance between sphingosine and sphingosine-1-phosphate is decisive for mast cell activation after Fcεreceptor I triggering", J Exp Med 190, pp. 1-8 (1999).
Quesniaux et al, "The novel immunosuppressant FTY720 induces peripheral lymphodepletion of both T- and B-cells in cynomolgus monkeys when given alone, with Cyclosporine Neoral (R) or with RAD", Transplant Immunology, 8: 177-187 (2000).
Reno et al., "Analysis of protein kinase C delta (PKCδ) expression in endometrial tumors", Hum Pathol, 39, pp. 21-29 (2008).
Reyland, "Protein kinase Cδ and apoptosis", Biochem Soc Trans 35, pp. 1001-1004 (2007).

Salesse et al., "BCR/ABL-mediated increased expression of multiple known and novel genes that may contribute to the pathogenesis of chronic myelogenous leukemia", Molecular Cancer Therapeutics, v. 2, p. 173-182 (2003).

Schonthal, A. H., "Role of serine/threonine protein phosphatase 2A in cancer", Cancer Lett. 170, pp. 1-13 (2001).

Seitz et al., "Effects of sphingosine 1-phosphate (S1P) and expression of S1P receptors in chronic lymphocyte leukemia (B-CLL): potential role in cell trafficking and survival", Experimental Hemaology, 33, p. 99 (2005).

Skerjanec et al., "FTY720, a novel immunomodulator in de novo kidney transplant patients: pharmacokinetics and exposure-response relationship. Journal of Clinical Pharmacology, 45: 1268-1278, 2005".

Stoetzer et al., "Drug-induced apoptosis in chronic lymphocytic leukemia. Leukemia : Official Journal of the Leukemia Society of America, Leukemia Research Fund, U.K, 13: 1873-1880, 1999".

Suleiman et al., "FTY720 prevents renal T-cell infiltration after ischemia/reperfusion injury. Transplantation Proceedings, 37: 373-374, 2005".

Suzuki et al., "A new immunosuppressant, FTY720, induces bcl-2-associated apoptotic cell death in human lymphocytes", Immunology, 89: 518-523 (1996).

Suzuki et al., "A novel immunosuppressant FTY720, with a unique mechanism of action, induces long-term graft acceptance in rat and dog allotransplantation", Transplantation, 61: pp. 200-205 (1996).

Suzuki et al., "Long-term graft acceptance in allografted rats and dogs by treatment with a novel immunosuppressant, FTY720. Transplantation Proceedings, 28: 1375-1376, 1996."

Suzuki et al., "Induction of lymphocyte apoptosis and prolongation of allograft survival by FTY720. Transplantation Proceedings, 28: 2049-2050, 1996."

Suzuki et al, "Immunosuppressive effect of a new drug, FTY720, on lymphocyte responses in vitro and cardiac allograft survival in rats. Transplant Immunology, 4: 252-255, 1996."

Takabe et al., ""Inside-out" signaling of sphingosine-1-phosphate: therapeutic targets", Pharmacol Rev 60, pp. 181-195 (2008).

International Search Report for PCT/US2006/010882, mailed Feb. 9, 2007.

International Search Report and Written Opinion from PCT/US10/31363 dated Jul. 13, 2010.

Office action from U.S. Appl. No. 12/302,953 dated Oct. 18, 2011.

Response from U.S. Appl. No. 12/302,953 dated Jan. 17, 2012.

Notice of Allowance from U.S. Appl. No. 12/302,953 daetd Apr. 23, 2012.

Office action from Australian Application No. 2007217810 dated Aug. 16, 2011.

Response from European Application No. 07751119.4 dated Feb. 17, 2010.

Extended European Search Report for European Application No. 07809273.1, dated Aug. 14, 2009.

Response to European Communication from 07809273.1 dated Sep. 22, 2010.

Ayllon et al., "Protein phosphatase 1 alpha is a Ras-activated Bad phosphatase that regulated interleukin-2 deprivation-induced apoptosis", The EMBO Journal, 19, pp. 2237-2246 (2000).

Azuma et al., "Marked prevention of tumor growth and metastasis by a novel immunosuppressive agent, FTY720, in mouse breast cancer models", Cancer Research, 62: 1410-1419 (2002).

Azuma et al. "Selective cancer cell apoptosis induced by FTY720; evidence for a Bcl-dependent pathway and impairment in ERK activity", Anticancer Research, 23: 3183-3193 (2003).

Baumhoer et al., "Glypican 3 expression in human nonneoplastic, preneoplastic, and neoplastic tissues", Am J Clin Pathol, 129, pp. 899-906 (2008).

Bellosillo et al., "Involvement of CED-3/ICE proteases in the apoptosis of B-chronic lymphocytic leukemia cells", Blood, 89: 3378-3384 (1997).

Boehler et al., "FTY720 alters the composition of T-lymphocyte subpopulations in the peripheral blood compartment of renal transplant patients", Transplantation Proceedings, 34: 2242-2243 (2002).

Bohler et al., "Pharmacodynamics of FTY720, the first member of a new class of immune-modulating therapeutics in transplantation medicine", International Journal of Clinical Pharmacology and Therapeutics, 41: 482-487 (2003).

Bohler et al., "FTY720 mediates apoptosis-independent lymphopenia in human renal allograft recipients: different effects on CD62L+ and CCR5+ T lymphocytes", Transplantation, 77: 1424-1432 (2004).

Braun, W.E, "Renal transplantation: basic concepts and evolution of therapy. J Clin Apher, 18: 141-152, 2003."

Brinkmann, V., "FTY720 alters lymphocyte homing and protects allografts without inducing general immunosuppression", Transplantation Proceedings, 33: 530-531 (2001).

Brinkmann et al., "The immune modulator FTY720 targets sphingosine 1-phosphate receptors", The Journal of Biological Chemistry, 277: 21453-21457 (2002).

Brinkmann, et al., "FTY720: targeting G-protein-coupled receptors for sphingosine 1-phosphate in transplantation and autoimmunity", Current Opinion in Immunology, 14: 569-575 (2002).

Brinkmann et al., "FTY720: sphingosine 1-phosphate receptor-1 in the control of lymphocyte egress and endothelial barrier function", American Journal of Transplantation; 4: 1019-1025 (2004).

Brinkmann, V. "FTY720: mechanism of action and potential benefit in organ transplantation", Yonsei Medical Journal, 45: 991-997 (2004).

Budde et al., First human trial of FTY720, a novel immunomodulator, in stable renal transplant patients. Journal of the American Society of Nephrology : JASN, 13: 1073-1083, 2002.

Budde et al., "Pharmacodynamics of single doses of the novel immunosuppressant FTY720 in stable renal transplant patients", American Journal of Transplantation; 3: 846-854 (2003).

Carbrera et al., "Review article: the management of hepatocellular carcinoma", Aliment. Pharmacol. Ther. 31, pp. 461-476 (2010).

Cattan, et al., "The C.B.17 scid mouse strain as a model for human disseminated leukaemia and myeloma in vivo. Leukemia Research, 18: 513-522, 1994".

Cheson et al., "National Cancer Institute-sponsored Working Group guidelines for chronic lymphocytic leukemia: revised guidelines for diagnosis and treatment. Blood, 87: 4990-4997, 1996".

Cheson et al., "Myelodysplastic syndromes standardized response criteria: further definition. Blood, 98: 1985, 2001".

Chiang et al., "Protein phosphatase 2A acivates the proapoptotic function of BAD in interleukin-3-dependent lymphoid cells by a mechanism requiring 14-3-3 dissociation", Blood, 1289-1297 (2001).

Chiba et al., "FTY720, a novel immunosuppressant possessing unique mechanisms. I. Prolongation of skin allograft survival and synergistic effect in combination with cyclosporine in rats", Transplantation Proceedings, 28, pp. 1056-1059 (1996).

Chua et al., "FTY720, a fungus metabolite, inhibits in vivo growth of androgen-independent prostate cancer", International Journal of Cancer, 117: 1039-1048 (2005).

Chueh et al., "Induction of tolerance toward rat cardiac allografts by treatment with allochimeric class I MHC antigen and FTY720. Transplantation, 64: 1407-1414, 1997".

Cohen et al., "Oral fingolimod or intramuscular interferon for relapsing multiple sclerosis", N Engl J Med 362, pp. 402-415 (2010).

D'Costa et al., "The proapoptosis tumor suppressor protein kinase C-δ is lost in human squamous cell carcinomas", Oncogene 25, pp. 378-386 (2006).

Dalen et al., "Alpha-tocopheryl succinate sensitises a T lymphoma cell line to TRAIL-induced apoptosis by suppressing NF-kappB activation", Br. J Cancer 88, pp. 153-158 (2003).

Dragun et al., "FTY720: early clinical experience. Transplantation Proceedings, 36: 544S-548S, 2004".

Dragun et al., "FTY720-induced lymphocyte homing modulates post-transplant preveration/reperfusion injury", Kidney Int 65, pp. 1076-1083 (2004).

Enosawa et al., "Induction of selective cell death targeting on mature T-lymphocytes in rats by a novel immunosuppressant, FTY720". Immunopharmacology, 34: 171-179 (1996).

Feschenko et al., "A novel cAMP-stimulated pathway in protein phosphatase 2A activation", J. Pharmacol. Exp. Ther. 302, pp. 111-118 (2002).

Ferguson, R., "FTY720 immunomodulation: optimism for improved transplant regimens. Transplantation Proceedings, 36: 549S-553S, 2004".

Fujino, et al., "Activation of caspases and mitochondria in FTY720-mediated apoptosis in human T cell line Jurkat", International Immunopharmacology, 1: 2011-2021 (2001).

Fujino et al., "Distinct pathways of apoptosis triggered by FTY720, etoposide, and anti-Fas antibody in human T-lymphoma cell line (Jurkat cells)", Journal of Pharmacology and Experimental Therapeutics, 300, p. 939-945 (2002).

Genini et al., "Nucleotide requirements for the in vitro activation of the apoptosis protein-activating factor-1-mediated caspase pathway. The Journal of Biological Chemistry, 275: 29-34, 2000".

Haynes et al., "Occurrence of pharmaceutically acceptable annions and cations in the Cambridge structural database", J Pharm Sci, 94, pp. 2111-2120 (2005).

International Search Report and Written Opinion from PCT/US07/12921 dated Dec. 12, 2007.

International Search Report and Written Opinion from PCT/US11/62304 dated Jun. 28, 2012.

Search Report from European Application No. 10765245.5 dated Jul. 11, 2012.

* cited by examiner

ANTIADHESION AGENTS

CONTINUING APPLICATION DATA

This application claims the benefit of U.S. Provisional Patent Application No. 61/170,316, filed Apr. 17, 2009, which is incorporated by reference herein.

GOVERNMENT FUNDING

The present invention was made with government support under Grant No. CA12250, awarded by the National Cancer Institute (NCI). The Government may have certain rights in this invention.

BACKGROUND

The therapeutic potential of α-tocopheryl succinate (a.k.a., vitamin E succinate; VES) in cancer treatment and prevention has been the focus of many recent investigation. See Neuzil et al., Mol Pharmacol 71, 1185-99 (2007) and Wang et al., Mol Nutr Food Res 50, 675-85 (2006). It is noteworthy that VES suppresses in vitro and in vivo tumor cell growth without incurring significant toxicity to normal cells. A growing body of evidence indicates that VES mediates its antitumor effect by perturbing a multitude of signaling pathways governing cancer cell growth, apoptosis, differentiation, angiogenesis, and metastasis. This broad spectrum of action in conjunction with low toxicity underlies the translational potential of VES in cancer treatment or prevention. Of various target mechanisms reported in the literature, the inhibitory effect of VES on cancer cell adhesion is especially noteworthy. Crispen et al., Prostate 67, 582-90 (2007) This is evident by the ability of α-tocopheryloxyacetic acid, a VES derivative with increased metabolic stability, to suppress breast tumor growth and to reduce lung metastasis in animal models. Hahn et al., Cancer Res, 66, 9374-8 (2006).

Substantial evidence indicates that cell adhesion is critical to the development of different aspects of the malignant phenotype of cancer cells, including survival, invasion, metastasis, and drug resistance. Consequently, targeting adhesion or its associated pathways represents a therapeutically relevant strategy to improve the clinical outcome of many solid and hematological malignancies. Although many humanized antibodies against different adhesion molecules have entered human trials, there exist few small-molecule cell adhesion-targeted agents.

SUMMARY OF THE INVENTION

One aspect of the invention provides compounds according to formula I:

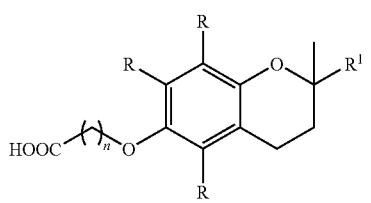

(I)

wherein R is independently selected from hydrogen and methyl; $R^1$ is selected from the group consisting of 4,8-dimethyl-non-1-enyl, 4,8-dimethyl-nonyl, non-1-enyl, nonanyl, non-8-enylnitrile, and nonanylnitrile groups; and n is an integer from 1 to 7, or a pharmaceutically acceptable salt thereof.

A further aspect of the invention provides a method of treating or preventing the development of cancer in a subject that includes administering a therapeutically effective amount of a composition including a compound of Formula (I) where the substituents are defined as described above, or a pharmaceutically acceptable salt thereof. Embodiments of this aspect of the invention may be used for treating adhesion-dependent cancer and metastatic cancer.

Another aspect of the invention provides a method of inhibiting cell adhesion in a subject in need thereof by administering a therapeutically effective amount of a pharmaceutical composition including a compound of Formula (I), where the substituents are defined as described above, or a pharmaceutically acceptable salt thereof.

Embodiments of the compositions or methods of the invention can include various subsets of the compounds described. For example in one embodiment, $R^1$ is selected from the group consisting of 4,8-dimethyl-non-1-enyl, non-1-enyl, and non-8-enylnitrile. In another embodiment, n is 1 or 2. In a further embodiment, n is 1 and $R^1$ is 4,8-dimethyl-non-1-enyl or 4,8-dimethyl-nonyl.

DETAILED DESCRIPTION OF THE INVENTION

Figure 1:
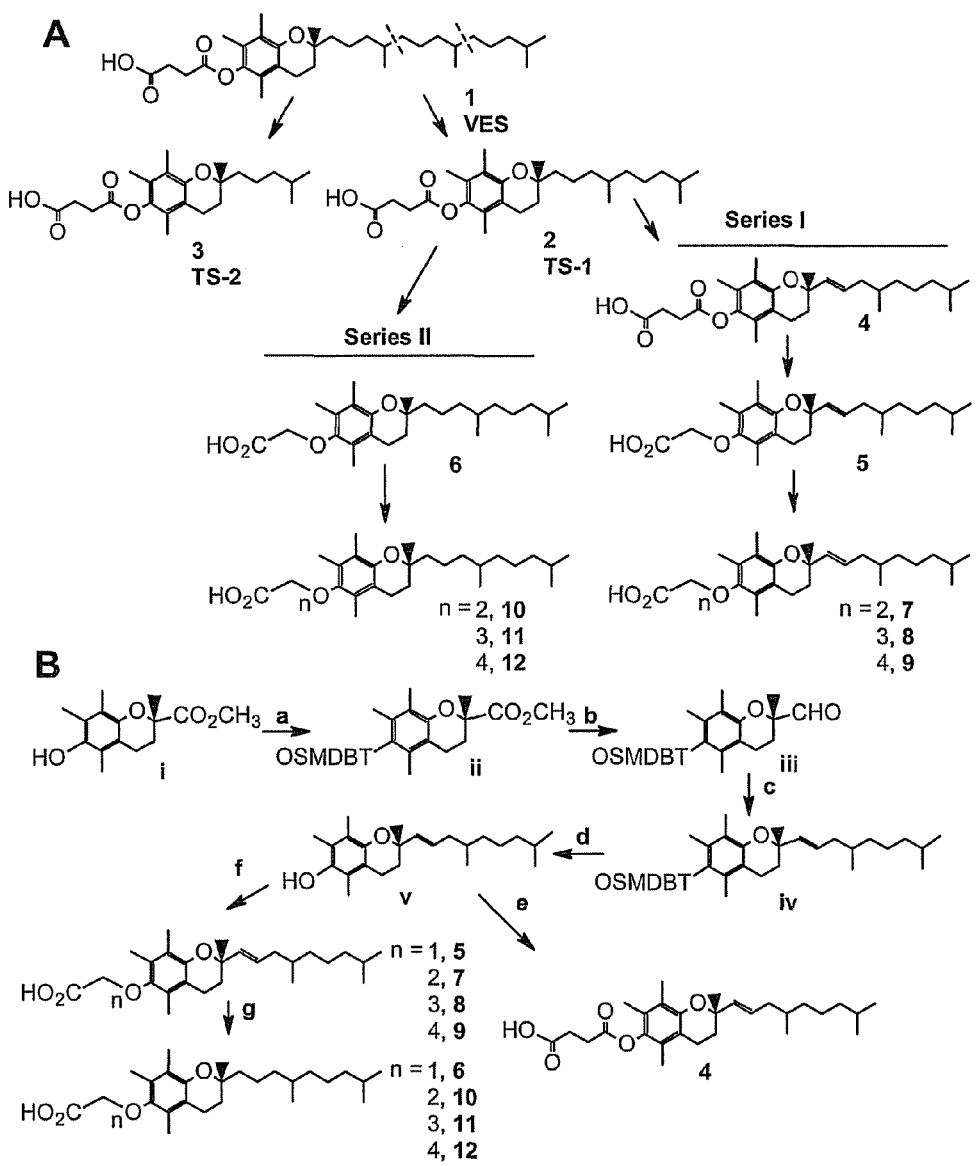
FIG. 1 provides (A) a schematic representation of the course of structural optimization of VES to develop antiadhesion agents and (B) a general synthetic procedure for VES derivatives.

The present invention provides potent small-molecule anti-adhesion agents developed based on the use of α-tocopheryl succinate (a.k.a., vitamin E succinate) as a scaffold. One of these anti-adhesion agents (compound 2) exhibits an order-of-magnitude higher potency than VES in blocking the adhesion of 4T1 metastatic breast cancer cells ($IC_{50}$, 0.6 uM versus 10 uM). Evidence indicates that the ability of vitamin E succinate derivatives to block cell adhesion and migration is attributable to their effect on disrupting focal adhesion kinase. From a therapeutic perspective, the high potency and unique mechanism of vitamin E succinate derivatives in inhibiting cell adhesion might have translational value for the treatment of cancers, and in particular metastatic cancers.

DEFINITIONS

The terminology as set forth herein is for description of the embodiments only and should not be construed as limiting of the invention as a whole. Unless otherwise specified, "a," "an," "the," and "at least one" are used interchangeably. Furthermore, as used in the description of the invention and the appended claims, the singular forms "a", "an", and "the" are inclusive of their plural forms, unless contraindicated by the context surrounding such.

The terms "comprising" and variations thereof do not have a limiting meaning where these terms appear in the description and claims.

As used herein, the term "organic group" is used for the purpose of this invention to mean a hydrocarbon group that is classified as an aliphatic group, cyclic group, or combination of aliphatic and cyclic groups (e.g., alkaryl and aralkyl groups). In the context of the present invention, suitable organic groups for vitamin E succinate derivatives are those that do not interfere with the vitamin E succinate derivatives' antiadhesion activity. In the context of the present invention, the term "aliphatic group" means a saturated or unsaturated linear or branched hydrocarbon group. This term is used to encompass alkyl, alkenyl, and alkynyl groups, for example.

As used herein, the terms "alkyl", "alkenyl", and the prefix "alk-" are inclusive of straight chain groups and branched chain groups and cyclic groups, e.g., cycloalkyl and cycloalkenyl. Unless otherwise specified, these groups contain from 1 to 20 carbon atoms, with alkenyl groups containing from 2 to 20 carbon atoms. In some embodiments, these groups have a total of at most 10 carbon atoms, at most 8 carbon atoms, at most 6 carbon atoms, or at most 4 carbon atoms. Lower alkyl groups are those including at most 6 carbon atoms. Examples of alkyl groups include haloalkyl groups and hydroxyalkyl groups. Cyclic groups can be monocyclic or polycyclic and preferably have from 3 to 10 ring carbon atoms.

The term "truncated side chain," as used herein, refers to a phytyl side chain of a tocopheryl succinate derivative that has been shortened by the removal of one or more isopranyl units. Such truncated side chains are alkyl groups including from 1 to 11 carbon atoms. Examples of truncated side chains include 4,8-dimethyl-non-1-enyl, 4,8-dimethyl-nonyl, non-1-enyl, and nonanyl groups.

Unless otherwise specified, "alkylene" and "alkenylene" are the divalent forms of the "alkyl" and "alkenyl" groups defined above. The terms, "alkylenyl" and "alkenylenyl" are used when "alkylene" and "alkenylene", respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-". Examples of suitable haloalkyl groups are chloromethyl, trifluoromethyl, and the like. A halo moiety can be chlorine, bromine, fluorine, or iodine.

The term "aryl" as used herein includes carbocyclic aromatic rings or ring systems. Examples of aryl groups include phenyl, naphthyl, biphenyl, anthracenyl, phenanthracenyl, fluorenyl and indenyl. Aryl groups may be substituted or unsubstituted.

Unless otherwise indicated, the term "heteroatom" refers to the atoms O, S, or N.

When a group is present more than once in any formula or scheme described herein, each group (or substituent) is independently selected, whether explicitly stated or not. For example, for the formula —C(O)—$NR_2$ each R group is independently selected.

As a means of simplifying the discussion and the recitation of certain terminology used throughout this application, the terms "group" and "moiety" are used to differentiate between chemical species that allow for substitution or that may be substituted and those that do not so allow for substitution or may not be so substituted. Thus, when the temi "group" is used to describe a chemical substituent, the described chemical material includes the unsubstituted group and that group with nonperoxidic O, N, S, Si, or F atoms, for example, in the chain as well as carbonyl groups or other conventional substituents. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tent-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyallyls, sulfoalkyls, etc. On the other hand, the phrase "alkyl moiety" is limited to the inclusion of only pure open chain saturated hydrocarbon alkyl substituents, such as methyl, ethyl, propyl, tert-butyl, and the like.

The invention is inclusive of the compounds described herein (including intermediates) in any of their pharmaceutically acceptable forms, including isomers (e.g., diastereomers and enantiomers), tautomers, salts, solvates, polymorphs, prodrugs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

Metastatic cancer, as used herein, is cancer that has the capacity to spread from one organ or part to another non-adjacent organ or part. When tumor cells metastasize, the new tumor is called a secondary or metastatic tumor, and its cells are like those in the original tumor. This means, for example, that, if breast cancer metastasizes to the lung, the secondary tumor is made up of abnormal breast cells, not of abnormal lung cells, and is called metastatic breast cancer rather than lung cancer. The primary tumor need not be detected, but rather can be "occult."

"Pharmaceutically acceptable" as used herein means that the compound or composition is suitable for administration to a subject to achieve the treatments described herein, without unduly deleterious side effects in light of the severity of the disease and necessity of the treatment.

"Inhibit" as used herein refers to the partial or complete elimination of a potential effect, while inhibitors are compounds that have the ability to inhibit.

Vitamin E Succinate Derivatives

Vitamin E succinate derivatives of the invention include compounds according to formula (I):

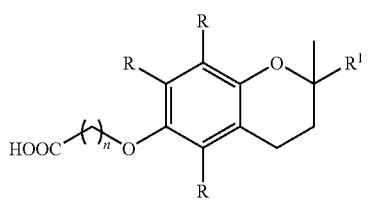

(I)

wherein R is independently selected from hydrogen and methyl; $R^1$ is selected from the group consisting of 4,8-dimethyl-non-1-enyl, 4,8-dimethyl-nonyl, non-1-enyl, nonanyl, non-8-enylnitrile, and nonanylnitrile groups; and n is an integer from 1 to 7. In additional embodiments, n may be 1, 1 or 2, or a range of integers from 1-3, 1-4, 1-5, or 1-6.

The Vitamin E succinate derivatives of the present invention have been shown and named herein without reference to stereochemistry. However, the compounds herein described have asymmetric centers. Unless otherwise indicated, all chiral, diastereomeric and racemic forms are included in the present invention. It will be appreciated that compounds of the present invention that contain asymmetrically substituted carbon atoms can be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated.

it is understood that vitamin E is [(2R)-2,5,7,8-Tetramethyl-2-[(4R,8R)-4,8,12-trimethyltidecyl]chroman-6-yl]acetate; i.e., a 2R isomer of the compounds shown, and that the 2R isomers may be preferred in some embodiments of the invention. Accordingly, the vitamin E succinate derivatives of the invention also include compounds according to formula (II):

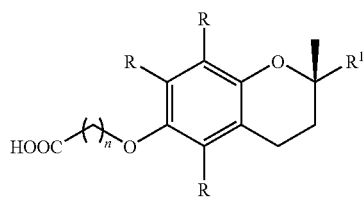

(II)

Wherein the various substituents are defined in the same manner as for formula (I).

In one embodiment, the vitamin E succinate derivatives of formula (I) are defined such that R is hydrogen and $R^1$ is 4,8-dimethyl-non-1-enyl. These compounds include compounds selected from the group consisting of [2-(4,8-dimethyl-non-1-enyl)-2-methyl-chroman-6-yloxy]-acetic acid, 3-[2-(4,8-dimethyl-non-1-enyl)-2-methyl-chroman-6-yloxy]-propionic acid, 4-[2-(4,8-dimethyl-non-1-enyl)-2-methyl-chroman-6-yloxy]-butyric acid, 5-[2-(4,8-dimethyl-non-1-enyl)-2-methyl-chroman-6-yloxy]-pentanoic acid, 6-[2-(4,8-dimethyl-non-1-enyl)-2-methyl-chroman-6-yloxy]-hexanoic acid, 7-[2-(4,8-dimethyl-non-1-enyl)-2-methyl-chroman-6-yloxy]-heptanoic acid, and 8-[2-(4,8-dimethyl-non-1-enyl)-2-methyl-chroman-6-yloxyl]-octanoic acid. Compounds in which R is hydrogen and $R^1$ is 4,8-dimethyl-non-1-enyl are shown below:

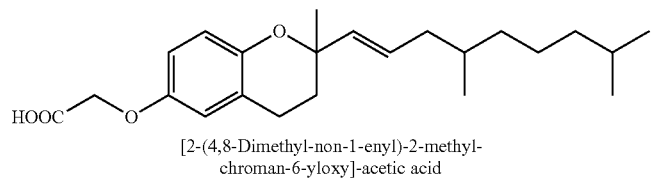

[2-(4,8-Dimethyl-non-1-enyl)-2-methyl-chroman-6-yloxy]-acetic acid

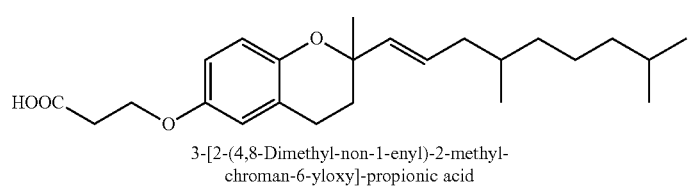

3-[2-(4,8-Dimethyl-non-1-enyl)-2-methyl-chroman-6-yloxy]-propionic acid

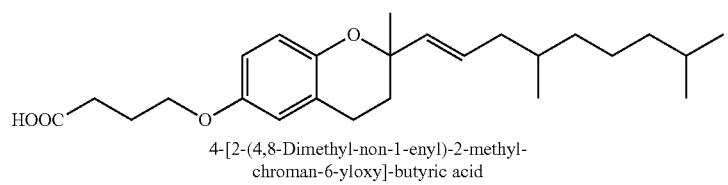

4-[2-(4,8-Dimethyl-non-1-enyl)-2-methyl-chroman-6-yloxy]-butyric acid

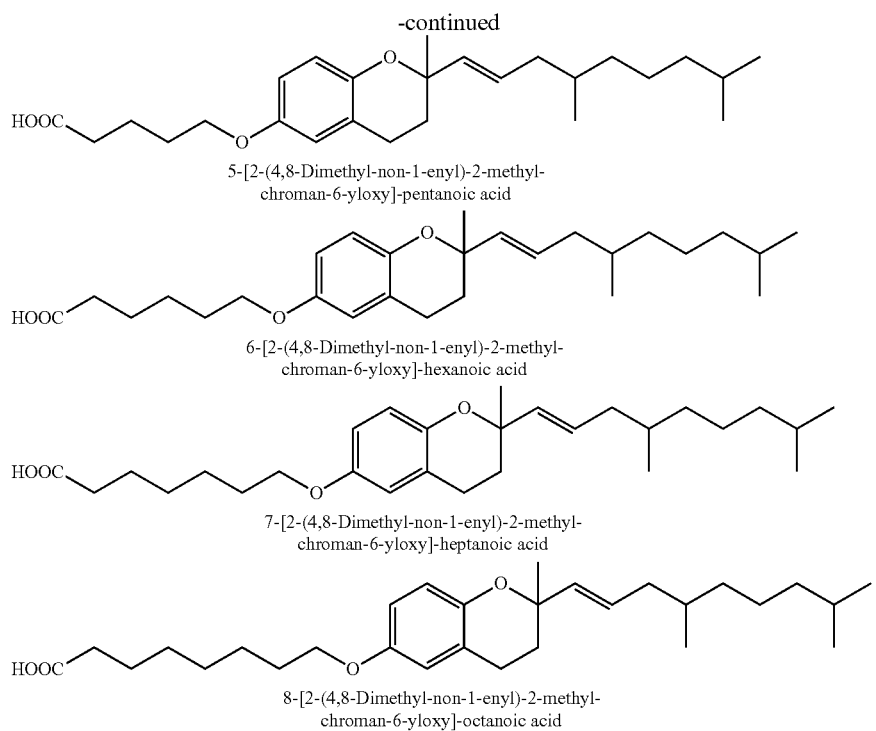

In another embodiment, the vitamin E succinate derivatives of formula (I) are defined such that R is hydrogen and $R^1$ is 4,8-dimethyl-nonyl. These compounds include compounds selected from the group consisting of [2-(4,8-dimethyl-nonyl)-2-methyl-chroman-6-yloxy]-acetic acid, 3-[2-(4,8-dimethyl-nonyl)-2-methyl-chroman-6-yloxy]-propionic acid, 4-[2-(4,8-dimethyl-nonyl)-2-methyl-chroman-6-yloxy]-butyric acid, 5-[2-(4,8-dimethyl-nonyl)-2-methyl-chroman-6-yloxy]-pentanoic acid, 6-[2-(4,8-dimethyl-nonyl)-2-methyl-chroman-6-yloxy]-hexanoic acid, 7-[2-(4,8-dimethyl-nonyl)-2-methyl-chroman-6-yloxy]-heptanoic acid, and 8-[2-(4,8-dimethyl-nonyl)-2-methyl-chroman-6-yloxy]-octanoic acid. Compounds in which R is hydrogen and $R^1$ is 4,8-dimethyl-nonyl are shown below:

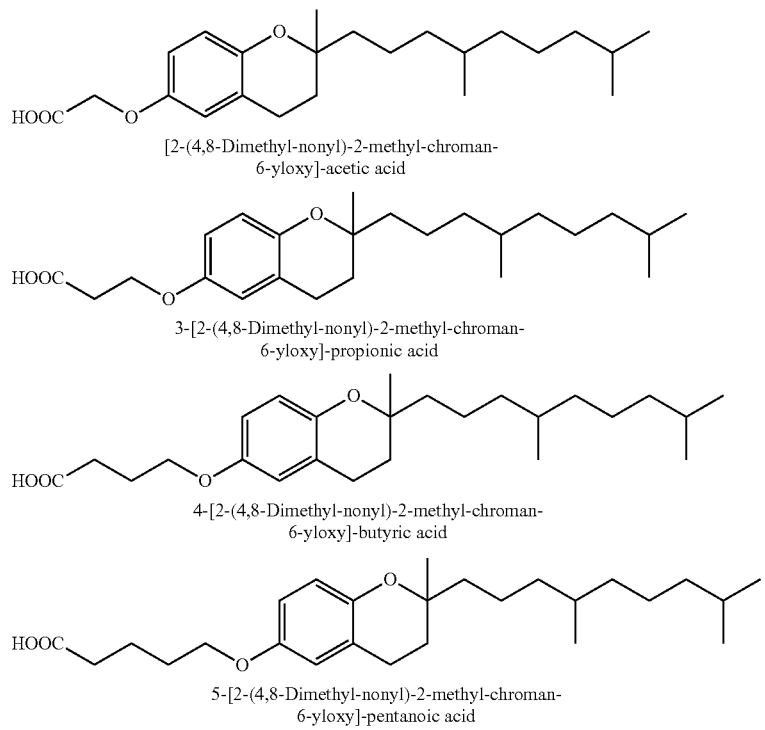

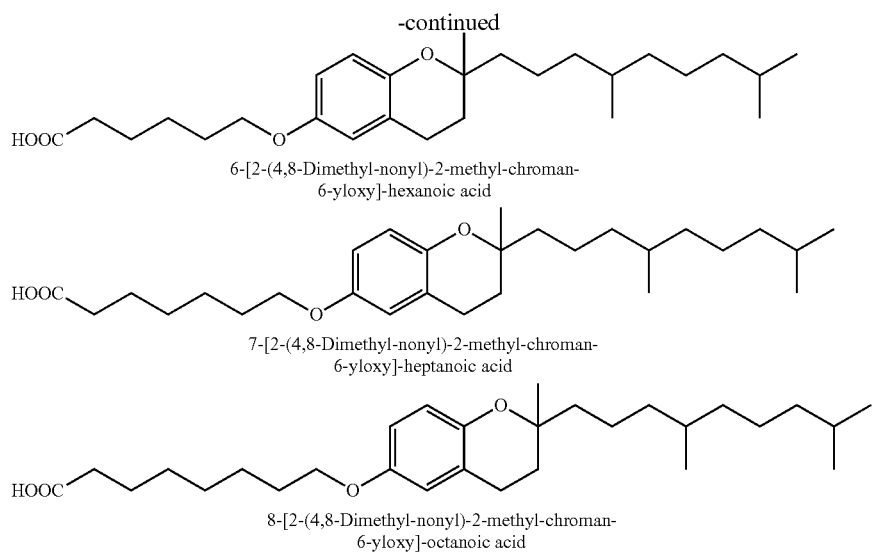

In another embodiment, the vitamin E succinate derivatives of formula (I) are defined such that R is hydrogen and $R^1$ is non-1-enyl. These compounds include compounds selected from the group consisting of (2-methyl-2-non-1-enyl-chroman-6-yloxy)-acetic acid, 3-(2-methyl-non-1-enyl-chroman-6-yloxy)-propionic acid, 4-(2-methyl-non-1-enyl-chroman-6-yloxy)-chroman-6-yloxy]-butyric acid, 5-(2-methyl-non-1-enyl-chroman-6-yloxy)-chroman-6-yloxy]-pentanoic acid, 6-(2-methyl-non-1-enyl-chroman-6-yloxy)-chroman-6-yloxy]-hexanoic acid, 7-(2-methyl-non-1-enyl-chroman-6-yloxy)-chroman-6-yloxy]-heptanoic acid, and 8-(2-methyl-non-1-enyl-chroman-6-yloxy)-chroman-6-yloxyl]-octanoic acid. Compounds in which R is hydrogen and $R^1$ is non-1-enyl are shown below:

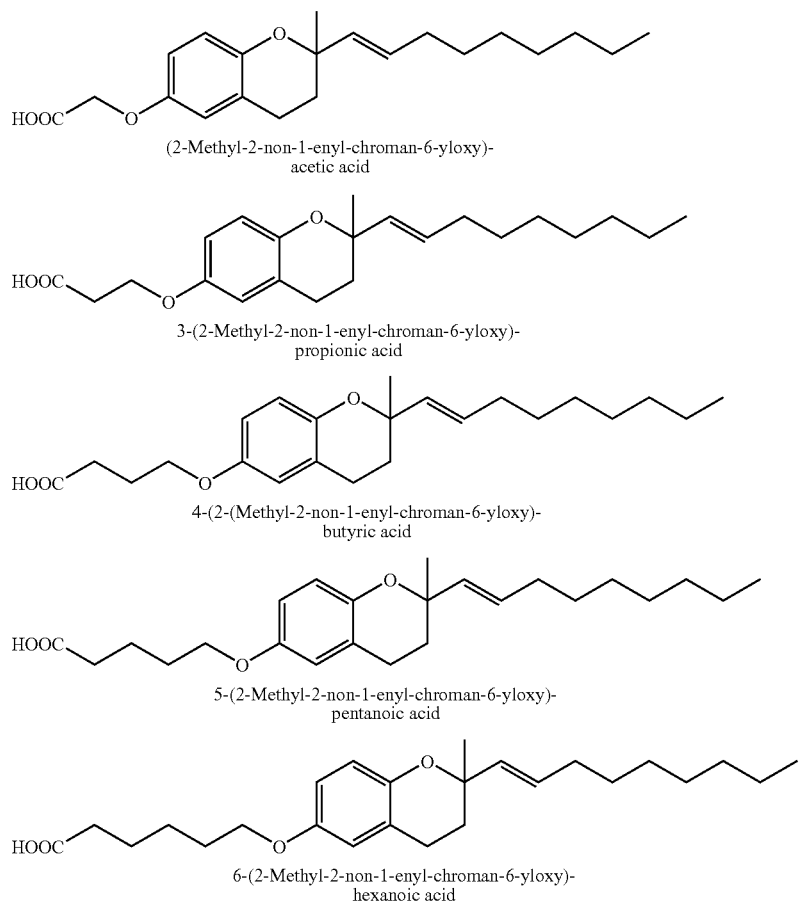

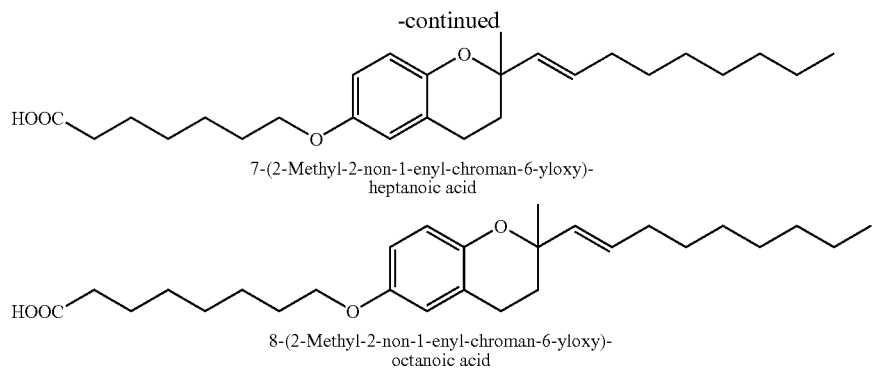

7-(2-Methyl-2-non-1-enyl-chroman-6-yloxy)-
heptanoic acid 8-(2-Methyl-2-non-1-enyl-chroman-6-yloxy)-
octanoic acid In another embodiment, the vitamin E succinate derivatives of formula (I) are defined such that R is hydrogen and $R^1$ is nonanyl. These compounds include compounds selected from the group consisting of (2-methyl-2-nonyl-chroman-6-yloxy)-acetic acid, 3-(2-methyl-nonyl-chroman-6-yloxy)-propionic acid, 4-(2-methyl-nonyl-chroman-6-yloxy)-chroman-6-yloxy]-butyric acid, 5-(2-methyl-nonyl-chroman-6-yloxy)-chroman-6-yloxy]-pentanoic acid, 6-(2-methyl-nonyl-chroman-6-yloxy)-chroman-6-yloxy]-hexanoic acid, 7-(2-methyl-nonyl-chroman-6-yloxy)-chroman-6-yloxy]-heptanoic acid, and 8-(2-methyl-nonyl-chroman-6-yloxy)-chroman-6-yloxy]-octanoic acid. Compounds in which R is hydrogen and $R^1$ is nonanyl are shown below:

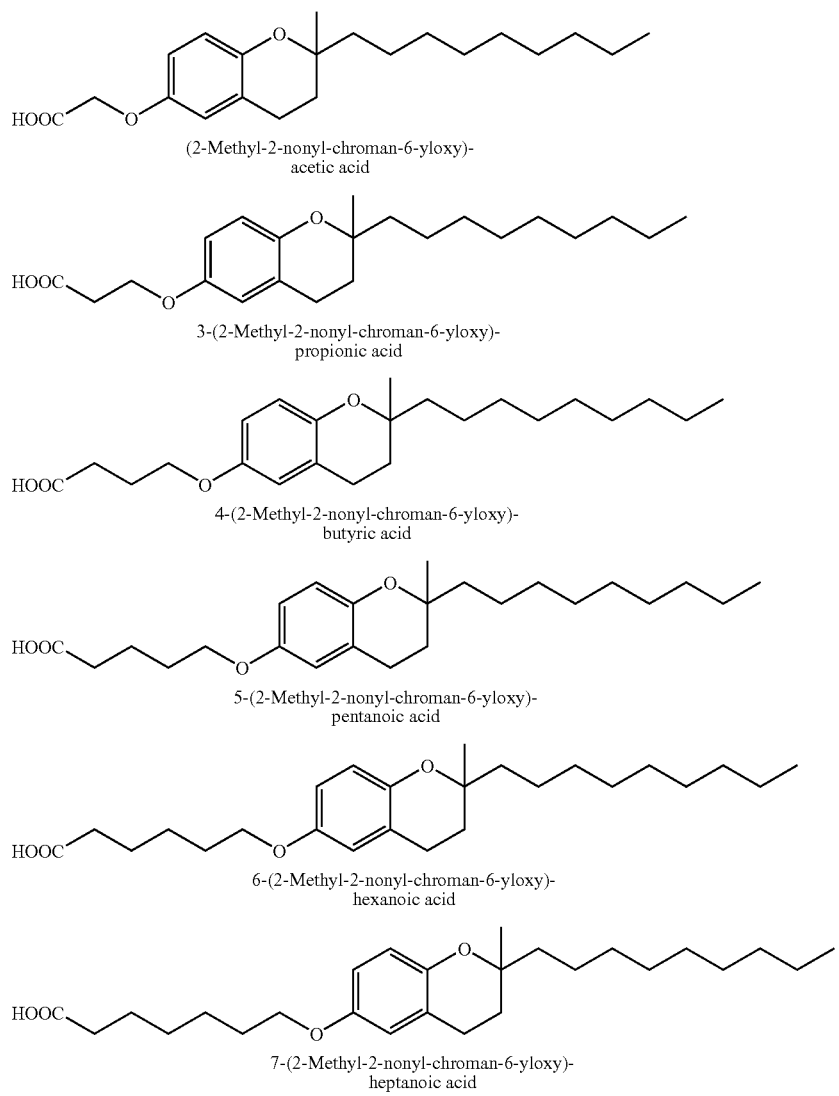

(2-Methyl-2-nonyl-chroman-6-yloxy)-
acetic acid 3-(2-Methyl-2-nonyl-chroman-6-yloxy)-
propionic acid 4-(2-Methyl-2-nonyl-chroman-6-yloxy)-
butyric acid 5-(2-Methyl-2-nonyl-chroman-6-yloxy)-
pentanoic acid 6-(2-Methyl-2-nonyl-chroman-6-yloxy)-
hexanoic acid 7-(2-Methyl-2-nonyl-chroman-6-yloxy)-
heptanoic acid

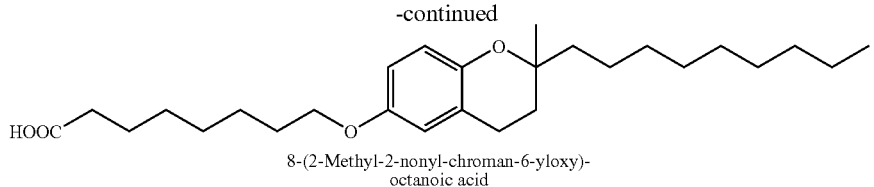

8-(2-Methyl-2-nonyl-chroman-6-yloxy)-
octanoic acid

In another embodiment, the vitamin E succinate derivatives of formula (I) are defined such that R is hydrogen and $R^1$ is non-8-enylnitrile. These compounds include compounds selected from the group consisting of [2-(8-cyno-oct-1-enyl)-2-methyl-chroman-6-yloxy]-acetic acid, 3-[2-(8-cyno-oct-1-enyl)-2-methyl-chroman-6-yloxy]-propionic acid, 4-[2-(8-cyno-oct-1-enyl)-2-methyl-chroman-6-yloxy]-butyric acid, 5-[2-(8-cyno-oct-1-enyl)-2-methyl-chroman-6-yloxy]-pentanoic acid, 6-[2-(8-cyno-oct-1-enyl)-2-methyl-chroman-6-yloxy]-hexanoic acid, 7-[2-(8-cyno-oct-1-enyl)-2-methyl-chroman-6-yloxy]-heptanoic acid, and 8-[2-(8-cyno-oct-1-enyl)-2-methyl-chroman-6-yloxy]-octanoic acid. Compounds in which R is hydrogen and $R^1$ is non-8-enylnitrile are shown below:

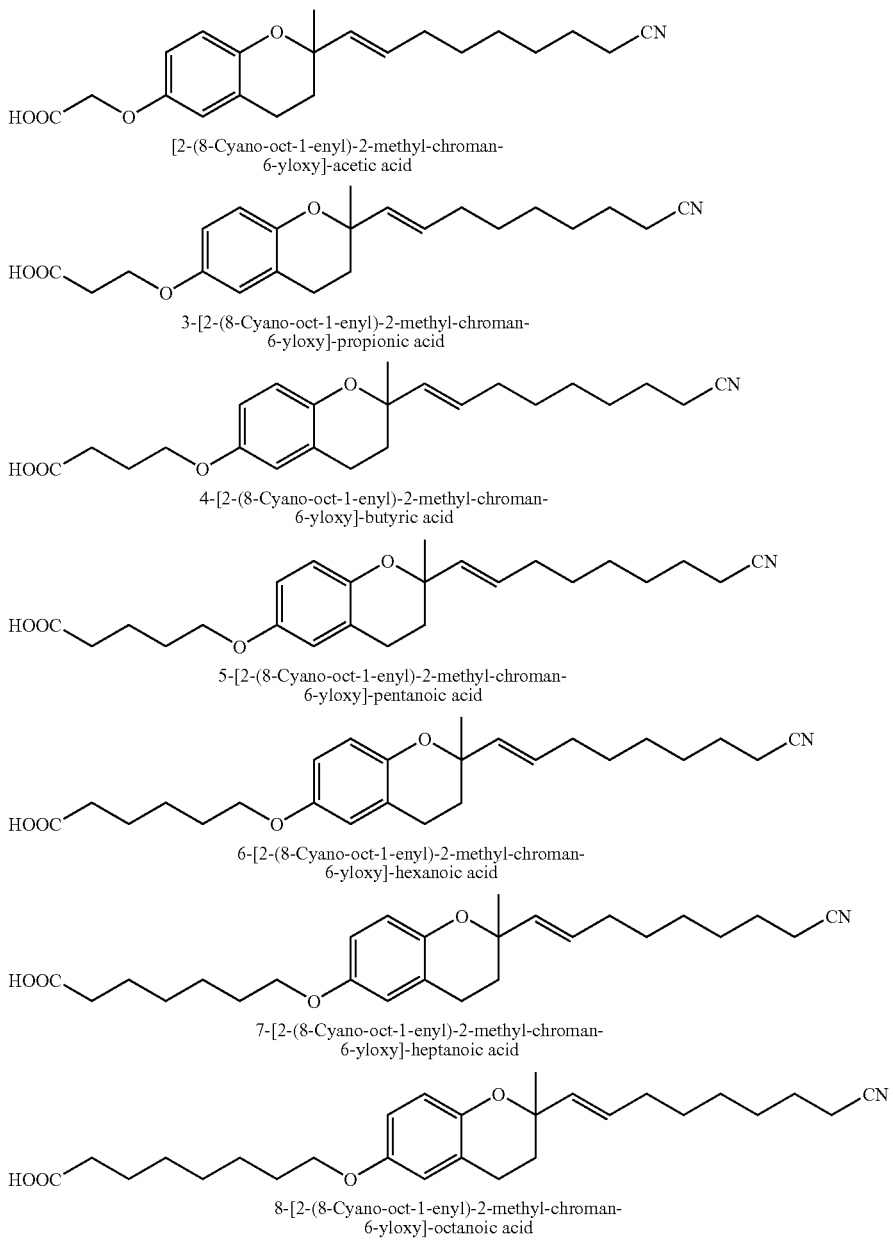

In another embodiment, the vitamin E succinate derivatives of formula (I) are defined such that R is hydrogen and $R^1$ is nonylnitrile. These compounds include compounds selected from the group consisting of [2-(8-cyno-octyl)-2-methyl-chroman-6-yloxy]-acetic acid, 3-[2-(8-cyno-octyl)-2-methyl-chroman-6-yloxy]-propionic acid, 4-[2-(8-cyno-octyl)-2-methyl-chroman-6-yloxy]-butyric acid, 5-[2-(8-cyno-octyl)-2-methyl-chroman-6-yloxy]-pentanoic acid, 6-[2-(8-cyno-oct-yl)-2-methyl-chroman-6-yloxy]-hexanoic acid, 7-[2-(8-cyno-octyl)-2-methyl-chroman-6-yloxy]-heptanoic acid, and 8-[2-(8-cyno-octyl)-2-methyl-chroman-6-yloxy]-octanoic acid. Compounds in which R is hydrogen and $R^1$ is nonylnitrile are shown below:

In another embodiment, the vitamin E succinate derivatives of formula (I) are defined such that R is methyl and $R^1$ is 4,8-dimethyl-non-1-enyl. These compounds include compounds selected from the group consisting of [2-(4,8-dimethyl-non-1-enyl)-2,5,7,8-tetramethyl-chroman-6-yloxy]-acetic acid, 3-[2-(4,8-dimethyl-non-1-enyl)-2,5,7,8-tetramethyl-chroman-6-yloxy]-propionic acid, 4-[2-(4,8-dimethyl-non-1-enyl)-2,5,7,8-tetramethyl-chroman-6-yloxy]-butyric acid, 5-[2-(4,8-dimethyl-non-1-enyl)-2,5,7,8-tetramethyl-chroman-6-yloxy]-pentanoic acid, 6-[2-(4,8-dimethyl-non-1-enyl)-2,5,7,8-tetramethyl-chroman-6-yloxy]-hexanoic acid, 7-[2-(4,8-dimethyl-non-1-enyl)-2,5,7,8-tetramethyl-chroman-6-yloxy]-heptanoic acid, and 8-[2-

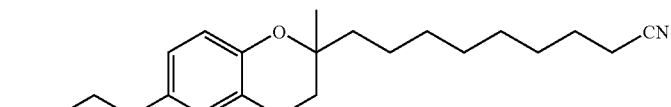

[2-(8-Cyano-octyl)-2-methyl-chroman-6-yloxy]-acetic acid

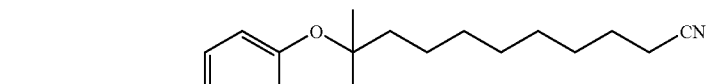

3-[2-(8-Cyano-octyl)-2-methyl-chroman-6-yloxy]-propionic acid

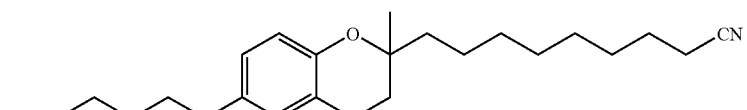

4-[2-(8-Cyano-octyl)-2-methyl-chroman-6-yloxy]-butyric acid

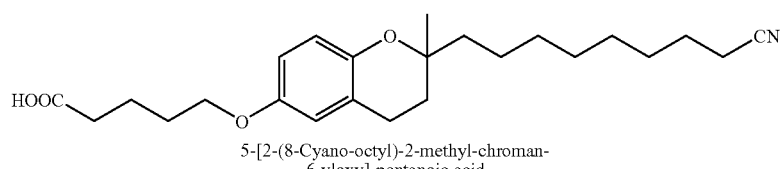

5-[2-(8-Cyano-octyl)-2-methyl-chroman-6-yloxy]-pentanoic acid

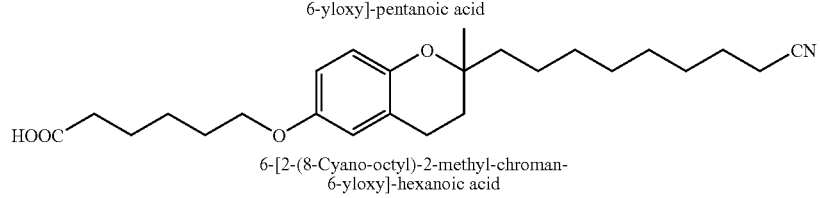

6-[2-(8-Cyano-octyl)-2-methyl-chroman-6-yloxy]-hexanoic acid

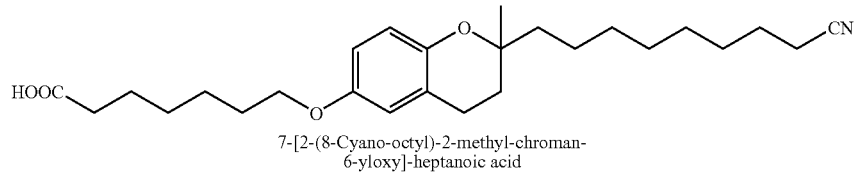

7-[2-(8-Cyano-octyl)-2-methyl-chroman-6-yloxy]-heptanoic acid

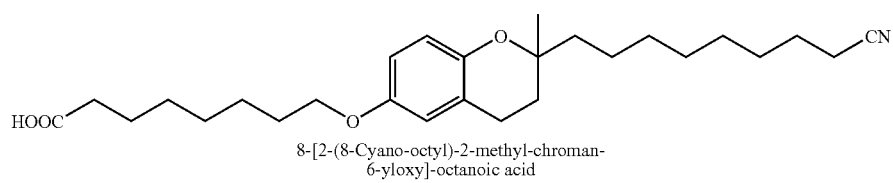

8-[2-(8-Cyano-octyl)-2-methyl-chroman-6-yloxy]-octanoic acid (4,8-dimethyl-non-1-enyl)-2,5,7,8-tetramethyl-chroman-6-yloxy]-octanoic acid. Compounds in which R is methyl and $R^1$ is 4,8-dimethyl-non-1-enyl are shown below:

In another embodiment, the vitamin E succinate derivatives of formula (I) are defined such that R is methyl and $R^1$ is 4,8-dimethyl-nonyl. These compounds include compounds

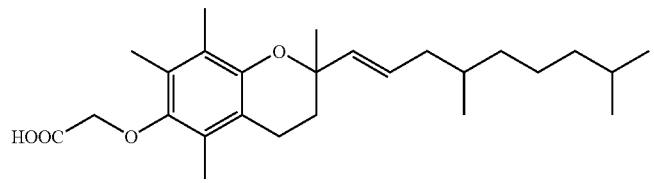

[2-(4,8-Dimethyl-non-1-enyl)-2,5,7,8-tetra methyl-chroman-6-yloxy]-acetic acid

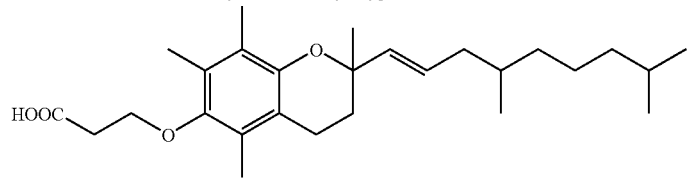

3-[2-(4,8-Dimethyl-non-1-enyl)-2,5,7,8-tetra methyl-chroman-6-yloxy]-propionic acid

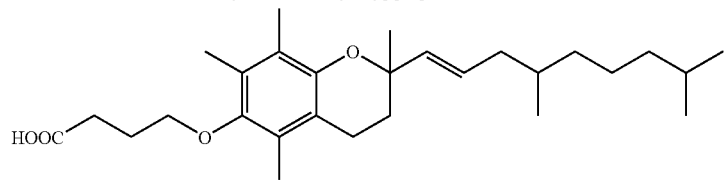

4-[2-(4,8-Dimethyl-non-1-enyl)-2,5,7,8-tetra methyl-chroman-6-yloxy]-butyric acid

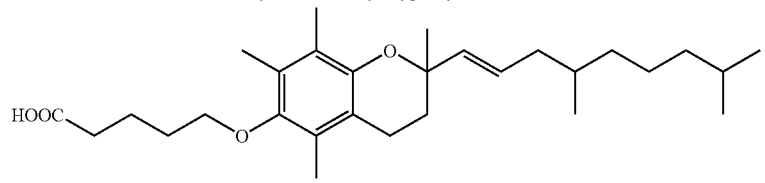

5-[2-(4,8-Dimethyl-non-1-enyl)-2,5,7,8-tetra methyl-chroman-6-yloxy]-pentanoic acid

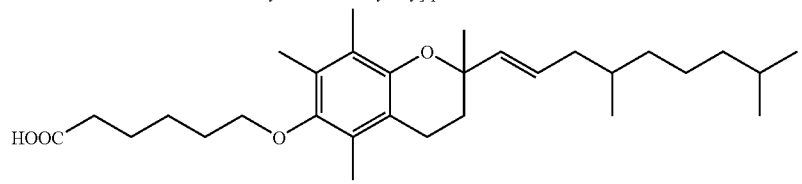

6-[2-(4,8-Dimethyl-non-1-enyl)-2,5,7,8-tetra methyl-chroman-6-yloxy]-hexanoic acid

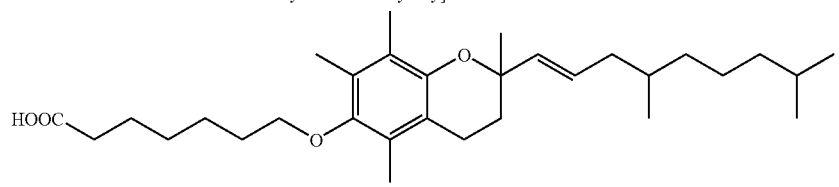

7-[2-(4,8-Dimethyl-non-1-enyl)-2,5,7,8-tetra methyl-chroman-6-yloxy]-heptanoic acid

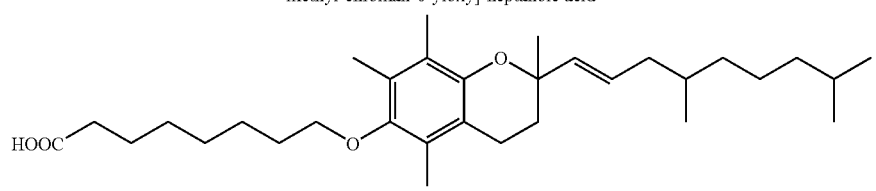

8-[2-(4,8-Dimethyl-non-1-enyl)-2,5,7,8-tetra methyl-chroman-6-yloxy]-octanoic acid selected from the group consisting of [2-(4,8-dimethyl-nonyl)-2,5,7,8-tetramethyl-chroman-6-yloxy]-acetic acid, 3-[2-(4,8-dimethyl-nonyl)-2,5,7,8-tetramethyl-chroman-6-yloxy]-propionic acid, 4-[2-(4,8-dimethyl-nonyl)-2,5,7,8-tetramethyl-chroman-6-yloxy]-butyric acid, 5-[2-(4,8-dimethyl-nonyl)-2,5,7,8-tetramethyl-chroman-6-yloxy]-pentanoic acid, 6-[2-(4,8-dimethyl-nonyl)-2,5,7,8-tetramethyl-chroman-6-yloxy]-hexanoic acid, 7-[2-(4,8-dimethyl-nonyl)-2,5,7,8-tetramethyl-chroman-6-yloxy]-heptanoic acid, and 8-[2-(4,8-dimethyl-nonyl)-2,5,7,8-tetramethyl-chroman-6-yloxy]-octanoic acid. Compounds in which R is methyl and $R^1$ is 4,8-dimethyl-nonyl are shown below:

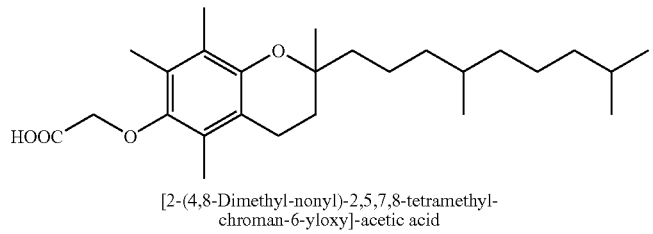

[2-(4,8-Dimethyl-nonyl)-2,5,7,8-tetramethyl-chroman-6-yloxy]-acetic acid

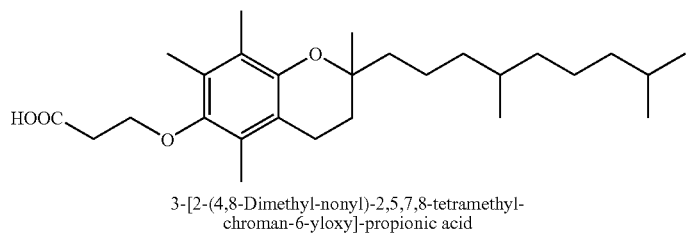

3-[2-(4,8-Dimethyl-nonyl)-2,5,7,8-tetramethyl-chroman-6-yloxy]-propionic acid

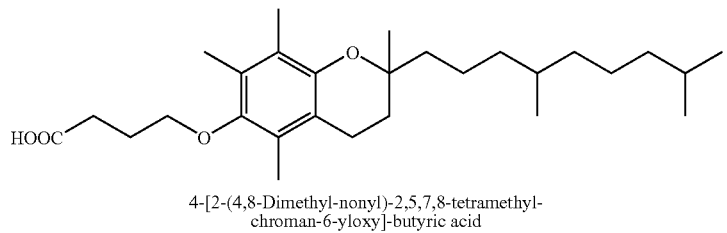

4-[2-(4,8-Dimethyl-nonyl)-2,5,7,8-tetramethyl-chroman-6-yloxy]-butyric acid

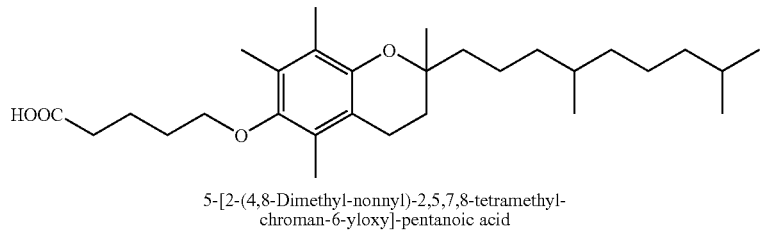

5-[2-(4,8-Dimethyl-nonnyl)-2,5,7,8-tetramethyl-chroman-6-yloxy]-pentanoic acid

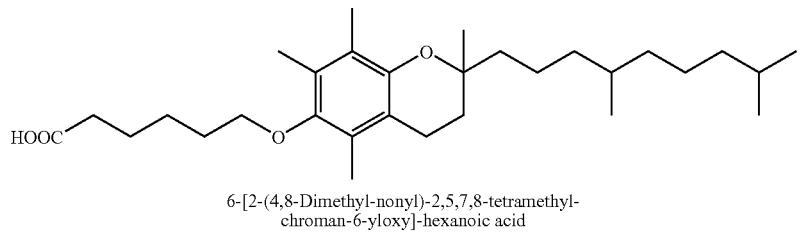

6-[2-(4,8-Dimethyl-nonyl)-2,5,7,8-tetramethyl-chroman-6-yloxy]-hexanoic acid

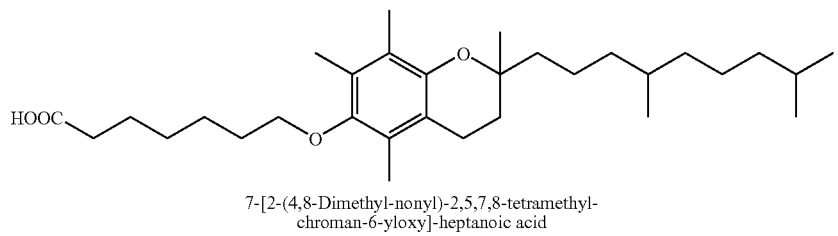

7-[2-(4,8-Dimethyl-nonyl)-2,5,7,8-tetramethyl-chroman-6-yloxy]-heptanoic acid

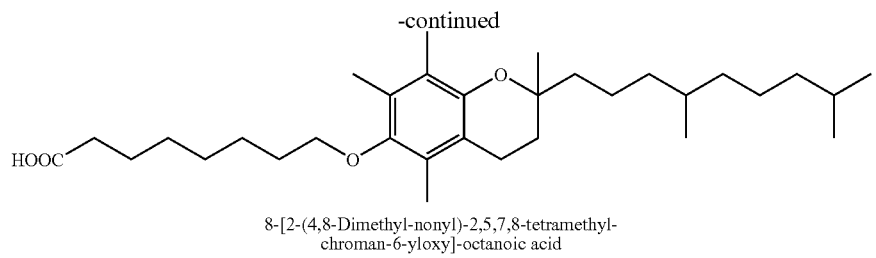

8-[2-(4,8-Dimethyl-nonyl)-2,5,7,8-tetramethyl-chroman-6-yloxy]-octanoic acid

In another embodiment, the vitamin E succinate derivatives of formula (I) are defined such that R is methyl and $R^1$ is non-1-enyl. These compounds include compounds selected from the group consisting of (2,5,7,8-tetramethyl-2-non-1-enyl-chroman-6-yloxy)-acetic acid, 3-(2,5,7,8-tetramethyl-non-1-enyl-chroman-6-yloxy)-propionic acid, 4-(2,5,7,8-tetramethyl-non-1-enyl-chroman-6-yloxy)-chroman-6-yloxy]-butyric acid, 5-(2,5,7,8-tetramethyl-non-1-enyl-chroman-6-yloxy)-chroman-6-yloxy]-pentanoic acid, 6-(2,5,7,8-tetramethyl-non-1-enyl-chroman-6-yloxy)-chroman-6-yloxy]-hexanoic acid, 7-(2,5,7,8-tetramethyl-non-1-enyl-chroman-6-yloxy)-chroman-6-yloxy]-heptanoic acid, and 8-(2,5,7,8-tetramethyl-non-1-enyl-chroman-6-yloxy)-chroman-6-yloxy]-octanoic acid. Compounds in which R is methyl and $R^1$ is non-1-enyl are shown below:

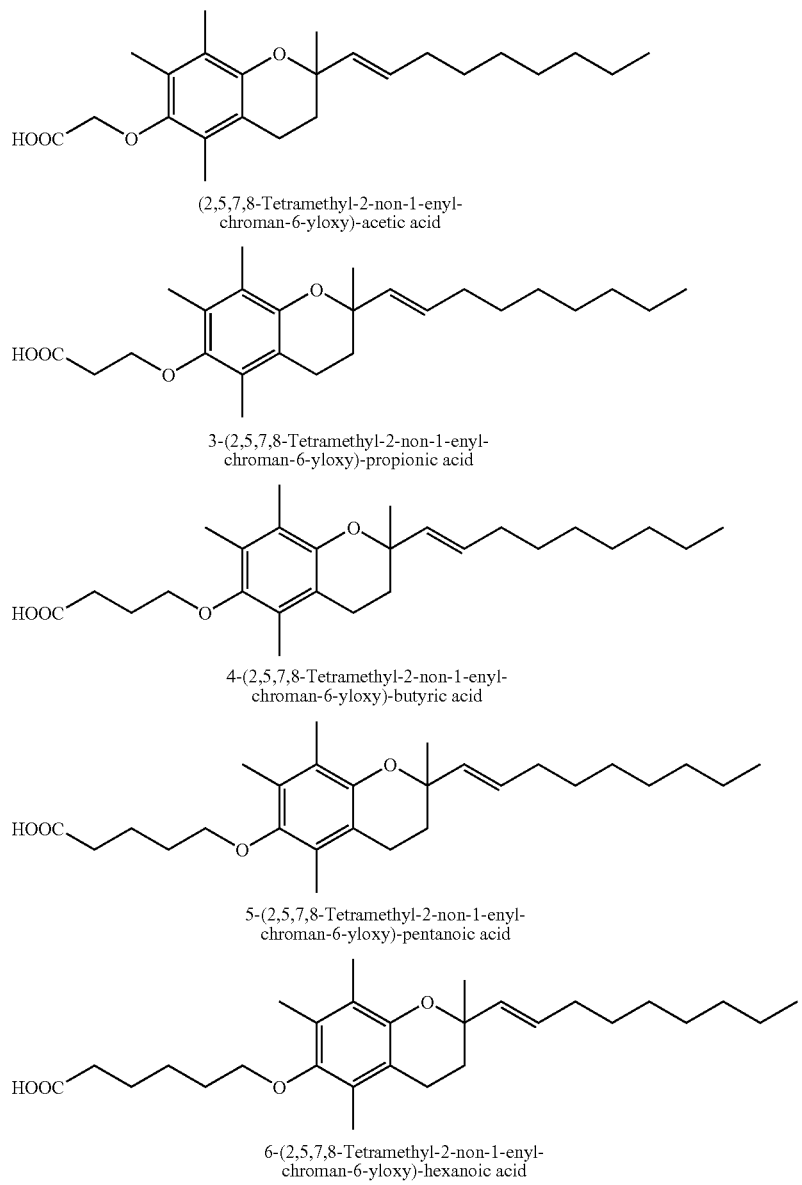

(2,5,7,8-Tetramethyl-2-non-1-enyl-chroman-6-yloxy)-acetic acid 3-(2,5,7,8-Tetramethyl-2-non-1-enyl-chroman-6-yloxy)-propionic acid 4-(2,5,7,8-Tetramethyl-2-non-1-enyl-chroman-6-yloxy)-butyric acid 5-(2,5,7,8-Tetramethyl-2-non-1-enyl-chroman-6-yloxy)-pentanoic acid 6-(2,5,7,8-Tetramethyl-2-non-1-enyl-chroman-6-yloxy)-hexanoic acid

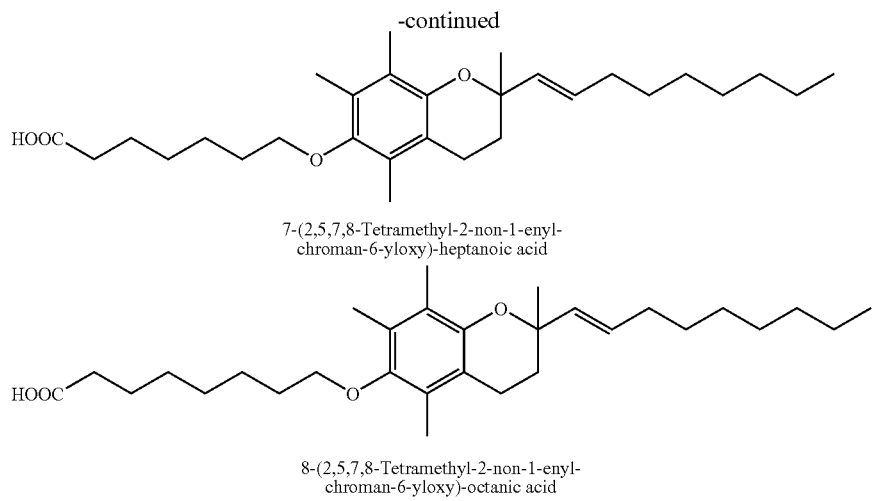

7-(2,5,7,8-Tetramethyl-2-non-1-enyl-
chroman-6-yloxy)-heptanoic acid 8-(2,5,7,8-Tetramethyl-2-non-1-enyl-
chroman-6-yloxy)-octanic acid In another embodiment, the vitamin E succinate derivatives of formula (I) are defined such that R is methyl and $R^1$ is nonanyl. These compounds include compounds selected from the group consisting of (2,5,7,8-teramethyl-2-nonyl-chroman-6-yloxy)-acetic acid, 3-(2,5,7,8-tetramethyl-nonyl-chroman-6-yloxy)-propionic acid, 4-(2,5,7,8-tetramethyl-nonyl-chroman-6-yloxy)-chroman-6-yloxy]-butyric acid, 5-(2,5,7,8-tetramethyl-nonyl-chroman-6-yloxy)-chroman-6-yloxy]-pentanoic acid, 6-(2,5,7,8-tetramethyl-nonyl-chroman-6-yloxy)-chroman-6-yloxy]-hexanoic acid, 7-(2,5,7,8-tetramethyl-nonyl-chroman-6-yloxy)-chroman-6-yloxy]-heptanoic acid, and 8-(2,5,7,8-tetramethyl-nonyl-chroman-6-yloxy)-chroman-6-yloxy]-octanoic acid. Compounds in which R is methyl and $R^1$ is nonanyl are shown below:

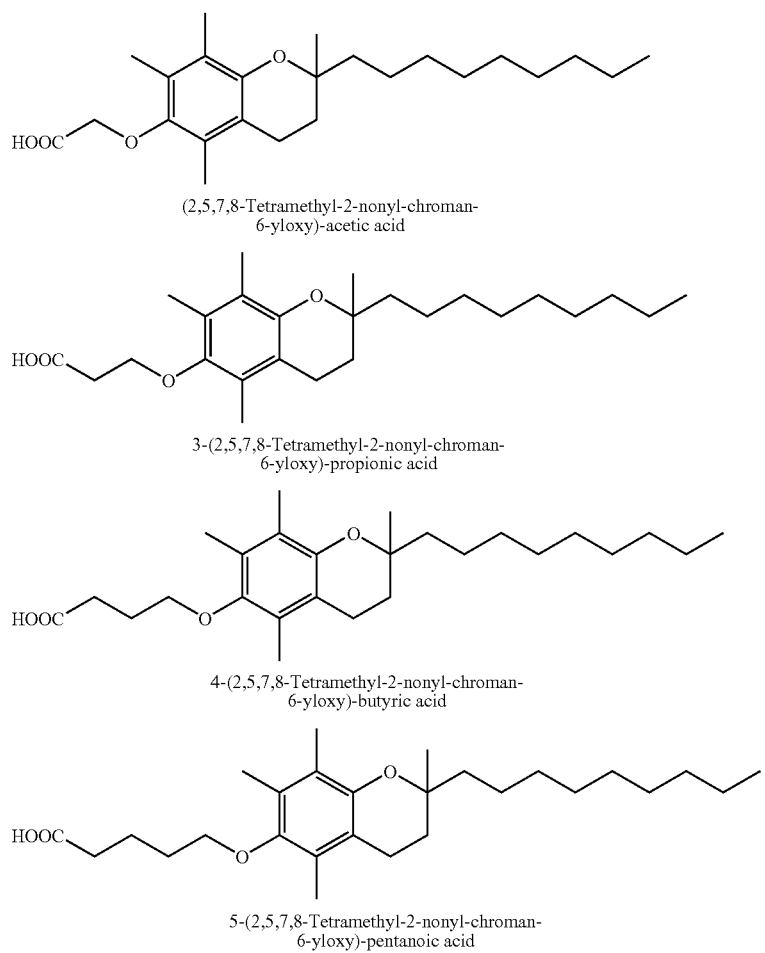

(2,5,7,8-Tetramethyl-2-nonyl-chroman-
6-yloxy)-acetic acid 3-(2,5,7,8-Tetramethyl-2-nonyl-chroman-
6-yloxy)-propionic acid 4-(2,5,7,8-Tetramethyl-2-nonyl-chroman-
6-yloxy)-butyric acid 5-(2,5,7,8-Tetramethyl-2-nonyl-chroman-
6-yloxy)-pentanoic acid

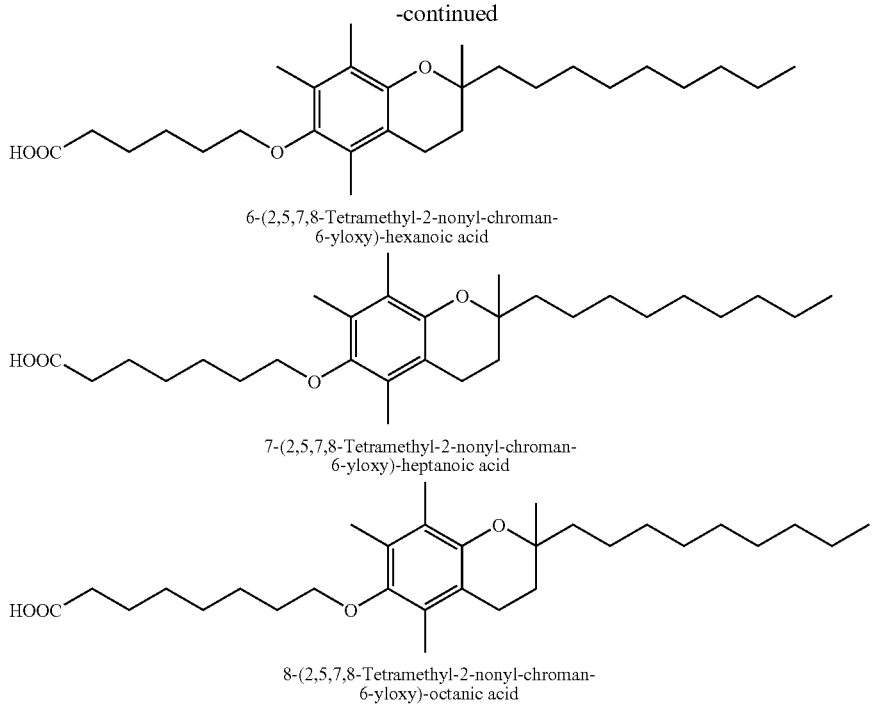

6-(2,5,7,8-Tetramethyl-2-nonyl-chroman-
6-yloxy)-hexanoic acid 7-(2,5,7,8-Tetramethyl-2-nonyl-chroman-
6-yloxy)-heptanoic acid 8-(2,5,7,8-Tetramethyl-2-nonyl-chroman-
6-yloxy)-octanic acid In another embodiment, the vitamin E succinate derivatives of formula (I) are defined such that R is methyl and $R^1$ is non-8-enylnitrile. These compounds include compounds selected from the group consisting of [2-(8-cyno-oct-1-enyl)-2,5,7,8-tetramethyl-chroman-6-yloxy]-acetic acid, 3-[2-(8-cyno-oct-1-enyl)-2,5,7,8-tetramethyl-chroman-6-yloxy]-propionic acid, 4-[2-(8-cyno-oct-1-enyl)-2,5,7,8-tetramethyl-chroman-6-yloxy]-butyric acid, 5-[2-(8-cyno-oct-1-enyl)-2,5,7,8-tetramethyl-chroman-6-yloxy]-pentanoic acid, 6-[2-(8-cyno-oct-1-enyl)-2,5,7,8-tetramethyl-chroman-6-yloxy]-hexanoic acid, 7-[2-(8-cyno-oct-1-enyl)-2,5,7,8-tetramethyl-chroman-6-yloxy]-heptanoic acid, and 8-[2-(8-cyno-oct-1-enyl)-2,5,7,8-tetramethyl-chroman-6-yloxy]octanoic acid. Compounds in which R is methyl and $R^1$ is non-8-enylnitrile are shown below:

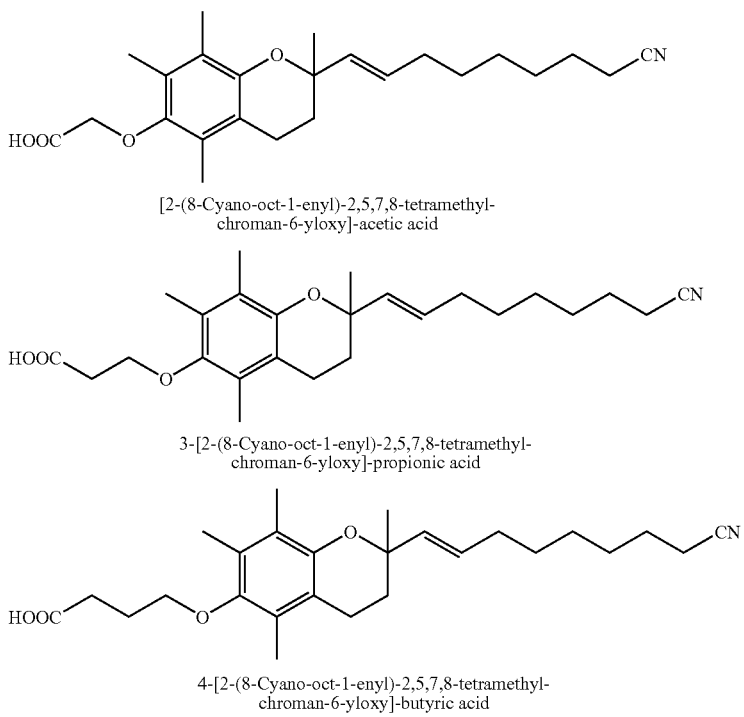

[2-(8-Cyano-oct-1-enyl)-2,5,7,8-tetramethyl-
chroman-6-yloxy]-acetic acid

3-[2-(8-Cyano-oct-1-enyl)-2,5,7,8-tetramethyl-
chroman-6-yloxy]-propionic acid

4-[2-(8-Cyano-oct-1-enyl)-2,5,7,8-tetramethyl-
chroman-6-yloxy]-butyric acid

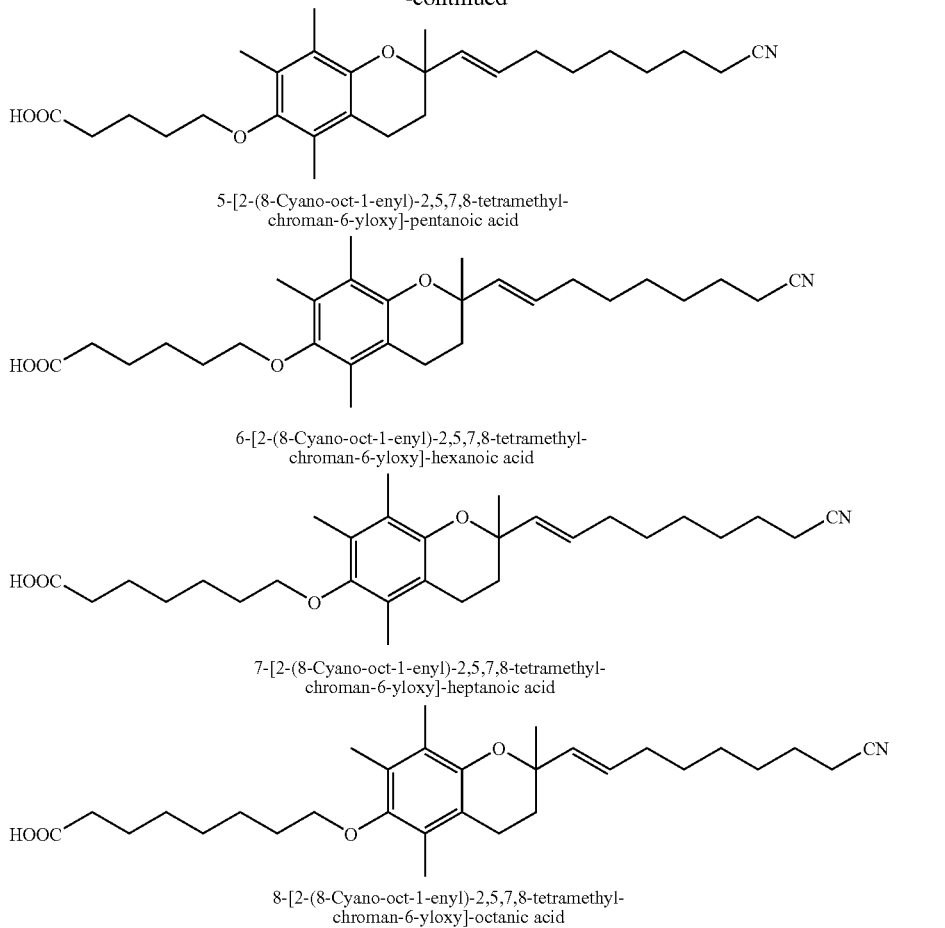

5-[2-(8-Cyano-oct-1-enyl)-2,5,7,8-tetramethyl-chroman-6-yloxy]-pentanoic acid

6-[2-(8-Cyano-oct-1-enyl)-2,5,7,8-tetramethyl-chroman-6-yloxy]-hexanoic acid

7-[2-(8-Cyano-oct-1-enyl)-2,5,7,8-tetramethyl-chroman-6-yloxy]-heptanoic acid

8-[2-(8-Cyano-oct-1-enyl)-2,5,7,8-tetramethyl-chroman-6-yloxy]-octanic acid

In another embodiment, the vitamin E succinate derivatives of formula (I) are defined such that R is methyl and $R^1$ is nonylnitrile. These compounds include compounds selected from the group consisting of [2-(8-cyno-octyl)-2,5,7,8-tetramethyl-chroman-6-yloxy]-acetic acid, 3-[2-(8-cyno-octyl)-2,5,7,8-tetramethyl-chroman-6-yloxy]-propionic acid, 4-[2-(8- cyno-octyl)-2,5,7,8-tetramethyl-chroman-6-yloxy]-butyric acid, 5-[2-(8-cyno-octyl)-2,5,7,8-tetramethyl-chroman-6-yloxy]-pentanoic acid, 6-[2-(8-cyno-oct-yl)-2,5,7,8-tetramethyl-chroman-6-yloxy]-hexanoic acid, 7-[2-(8-cyno-octyl)-2,5,7,8-tetramethyl-chroman-6-yloxy]-heptanoic acid, and 8-[2-(8-cyno-octyl)-2,5,7,8-tetramethyl-chroman-6-yloxy]-octanoic acid. Compounds in which R is methyl and $R^1$ is nonylnitrile are shown below:

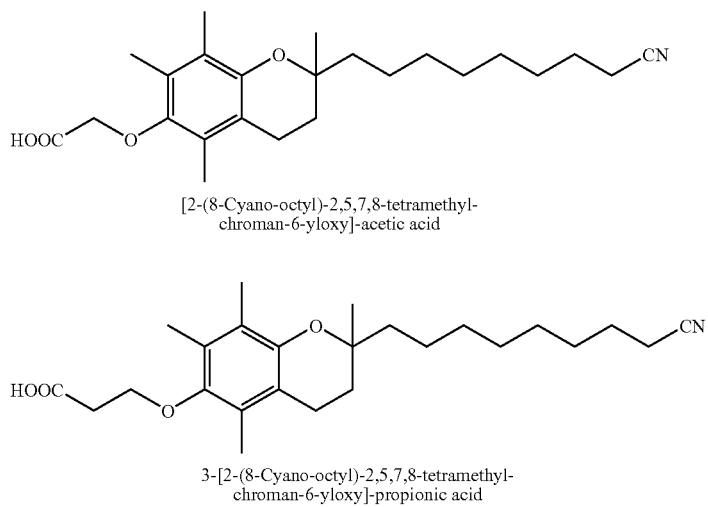

[2-(8-Cyano-octyl)-2,5,7,8-tetramethyl-chroman-6-yloxy]-acetic acid

3-[2-(8-Cyano-octyl)-2,5,7,8-tetramethyl-chroman-6-yloxy]-propionic acid

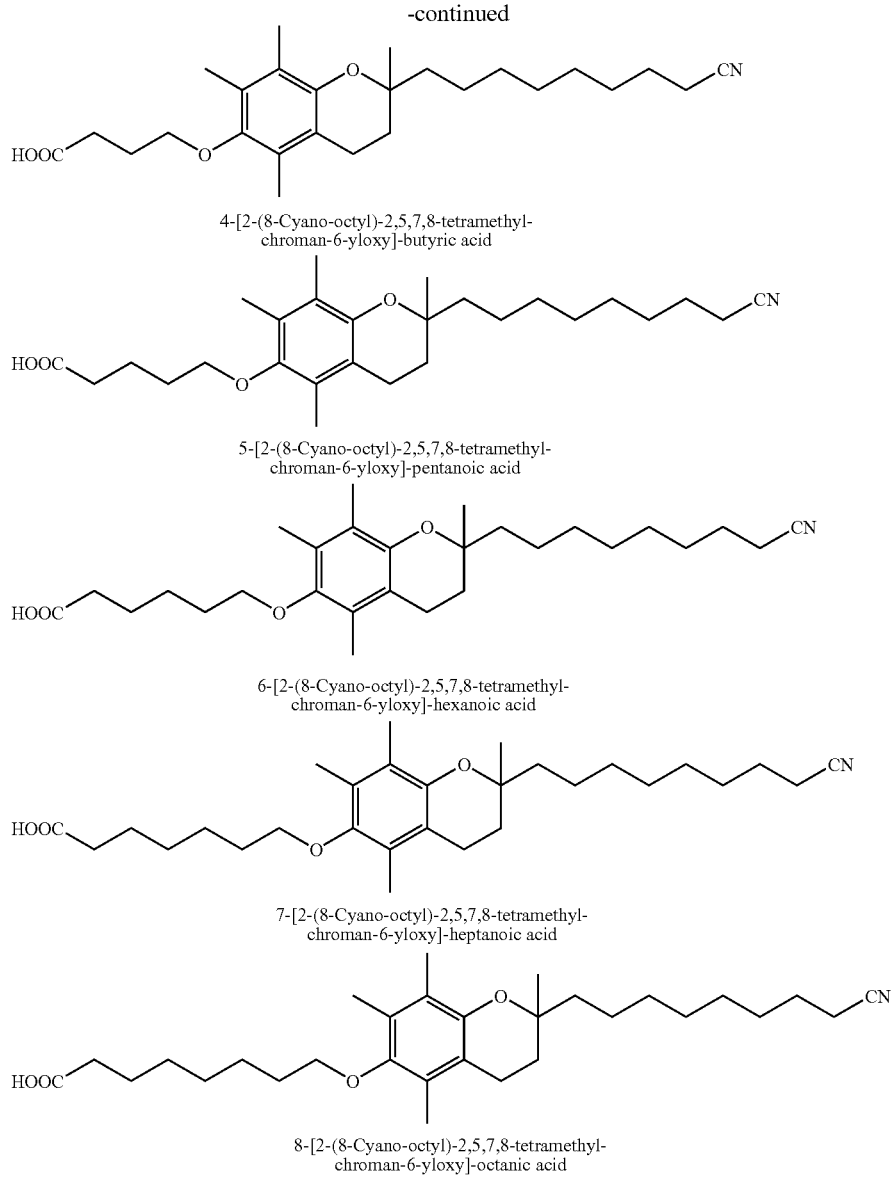

4-[2-(8-Cyano-octyl)-2,5,7,8-tetramethyl-chroman-6-yloxy]-butyric acid

5-[2-(8-Cyano-octyl)-2,5,7,8-tetramethyl-chroman-6-yloxy]-pentanoic acid

6-[2-(8-Cyano-octyl)-2,5,7,8-tetramethyl-chroman-6-yloxy]-hexanoic acid

7-[2-(8-Cyano-octyl)-2,5,7,8-tetramethyl-chroman-6-yloxy]-heptanoic acid

8-[2-(8-Cyano-octyl)-2,5,7,8-tetramethyl-chroman-6-yloxy]-octanic acid

Candidate agents may be tested in animal models. Typically, the animal model is one for the study of cancer. The study of various cancers in animal models (for instance, mice) is a commonly accepted practice for the study of human cancers. For instance, the nude mouse model, where human tumor cells are injected into the animal, is commonly accepted as a general model useful for the study of a wide variety of cancers (see, for instance, Polin et al., Investig. New Drugs, 15, p. 99-108 (1997)). Results are typically compared between control animals treated with candidate agents and the control littermates that did not receive treatment. Transgenic animal models are also available and are commonly accepted as models for human disease (see, for instance, Greenberg et al., Proc. Natl. Acad. Sci. USA, 92, p. 3439-3443 (1995)). Candidate agents can be used in these animal models to determine if a candidate agent decreases one or more of the symptoms associated with the cancer, including, for instance, cancer metastasis, cancer cell motility, cancer cell invasiveness, or combinations thereof.

Treatment Using Vitamin E Succinate Derivatives

The present invention provides methods for treating or preventing the development of cancer in a subject using vitamin E succinate derivatives. Cancer is a disease of abnormal and excessive cell proliferation. Cancer is generally initiated by an environmental insult or error in replication that allows a small fraction of cells to escape the normal controls on proliferation and increase their number. The damage or error generally affects the DNA encoding cell cycle checkpoint controls, or related aspects of cell growth control such as tumor suppressor genes. As this fraction of cells proliferates, additional genetic variants may be generated, and if they provide growth advantages, will be selected in an evolutionary fashion. Cells that have developed growth advantages but have not yet become fully cancerous are referred to as pre-cancerous cells. Cancer results in an increased number of cancer cells in a subject. These cells may form an abnormal mass of cells called a tumor, the cells of which are referred to as tumor cells. The overall amount of tumor cells in the body of a subject is referred to as the tumor load. Tumors can be either benign or malignant. A benign tumor contains cells that are proliferating but remain at a specific site. The cells of a malignant tumor, on the other hand, can invade and destroy nearby tissue and spread to other parts of the body through a process referred to as metastasis.

Cancer is generally named based on its tissue of origin. There are several main types of cancer. Carcinoma is cancer that begins in the skin or in tissues that line or cover internal organs. Sarcoma is cancer that begins in bone, cartilage, fat, muscle, blood vessels, or other connective or supportive tissue. Leukemia is cancer that starts in blood-forming tissue such as the bone marrow, and causes large numbers of abnormal blood cells to be produced and enter the bloodstream. Lymphoma and multiple myeloma are cancers that begin in the cells of the immune system.

The vitamin E succinate derivatives of the present invention can be used to treat various types of cancer and precancers. For example, the vitamin E succinate derivatives can be used to treat adhesion-dependent cancers. The vitamin E succinate derivatives can also be used to treat metastatic cancer.

Loss of normal cellular adhesion is an important feature of cancer development. Disruption of adhesion leads to increased cell motility and potential invasiveness of cells through the extracellular matrix (ECM). Metastasis is characterized by a modification of normal adhesion that allows cancer cells to invade and leave the site of origin and subsequently adhere to other sites. However, cell adhesion is also involved in other aspects of cancer, such as tumor cell survival, tissue invasion, and drug resistance. See Schmidmaier et al., Curr Med Chem 15, 978-90 (2008). Adhesion-dependent cancers are forms of cancer in which adhesion plays an important role in the cancer pathology.

The vitamin E succinate derivatives of the invention can also be used as antiadhesion agents. Anti-adhesion agents, as used herein, refers to agents that inhibit cell adhesion, rather than tissue adhesion overall. While not intending to be bound by theory, the vitamin E succinate derivatives of the invention are believed to inhibit cell adhesion by inducing focal adhesion kinase (FAK) degradation.

While antiadhesion agents can be used for cancer treatment, they can also be used to treat a wide variety of other diseases and disorders, particularly those involving cell adhesion and/or cell migration. For example, cell adhesion plays an important role in the infiltration of leukocytes that produce mediators of angiogenesis at an inflammatory site. Diseases and disorders that can be treated using antiadhesion agents include thromboembolic disorders, inflammation, inflammatory bowel disease and other autoimmune diseases, rheumatoid arthritis, asthma, allergies, adult respiratory distress syndrome, graft versus host disease, organ transplantation, septic shock, psoriasis, eczema, contact dermatitis, osteoporosis, osteoarthritis, atherosclerosis, diabetic retinopathy, ocular vasculopathies, bone degradation, diabetic retinopathy, macular degeneration, and wound healing.

Treatment, as used herein, encompasses the administration of vitamin E succinate derivatives to a subject that is already afflicted by cancer (i.e., non-prophylactic treatment). In one embodiment of therapeutic administration, administration of the vitamin E succinate derivatives is effective to eliminate the cancer; in another embodiment, administration of the vitamin E succinate derivatives is effective to decrease the severity of the cancer or lengthen the lifespan of the subject so afflicted. Treatment includes improvement in the condition through lessening or suppression of at least one symptom and/or delaying in progression of the disease. The subject is preferably a mammal, such as a domesticated farm animal (e.g., cow, horse, pig) or pet (e.g., dog, cat). More preferably, the subject is a human.

Preventing the development of cancer, as used herein, encompasses the prophylactic (i.e., preventive) treatment of cancer. Vitamin E succinate derivatives of the invention can, for example, be administered prophylactically to a subject in advance of the occurrence of cancer. Prophylactic administration is effective to decrease the likelihood of the subsequent occurrence of cancer in the subject, or decrease the severity of cancer that subsequently occurs.

Administration and Formulation of Vitamin E Succinate Derivatives

The present invention also provides pharmaceutical compositions that include vitamin E succinate derivatives according to formula I as an active ingredient, and a pharmaceutically acceptable liquid or solid carrier or carriers, in combination with the active ingredient. Any of the vitamin E succinate derivatives described above as being suitable for the treatment of cancer can be included in pharmaceutical compositions of the invention.

The vitamin E succinate derivatives can be administered without modification, or can be administered as pharmaceutically acceptable salts. Pharmaceutically acceptable salt refers to the relatively non-toxic, inorganic and organic acid addition salts of the vitamin E succinate derivatives. These salts can be prepared in situ during the final isolation and purification of the vitamin E succinate derivative, or by separately reacting a purified vitamin E succinate derivative with a suitable organic or inorganic counterion, and isolating the salt thus formed. Representative cationic counterions suitable for use with vitamin E succinate derivative anions include ammonium, arginine, diethylamine, ethylenediamine, piperazine, and the like. (See, for example, Handbook of Pharmaceutical Salts: Properties, Selection, and Use, P. H. Stahl and C. G. Wermuth (Eds), Wiley (2008)).

The pharmaceutical compositions include one or more vitamin E succinate derivatives together with one or more of a variety of physiological acceptable carriers for delivery to a patient, including a variety of diluents or excipients known to those of ordinary skill in the art. For example, for parenteral administration, isotonic saline is preferred. For topical administration, a cream, including a carrier such as dimethylsulfoxide (DMSO), or other agents typically found in topical creams that do not block or inhibit activity of the peptide, can be used. Other suitable carriers include, but are not limited to, alcohol, phosphate buffered saline, and other balanced salt solutions.

The formulations may be conveniently presented in unit dosage form and may be prepared by any of the methods well known in the art of pharmacy. Preferably, such methods include the step of bringing the active agent into association with a carrier that constitutes one or more accessory ingredients. In general, the formulations are prepared by uniformly and intimately bringing the active agent into association with a liquid carrier, a finely divided solid carrier, or both, and then, if necessary, shaping the product into the desired formulations. The methods of the invention include administering to a subject, preferably a mammal, and more preferably a human, the composition of the invention in an amount effective to produce the desired effect. The vitamin E succinate derivatives can be administered as a single dose or in multiple doses. Useful dosages of the active agents can be determined by comparing their in vitro activity and the in vivo activity in animal models. Methods for extrapolation of effective dosages in mice, and other animals, to humans are known in the art; for example, see U.S. Pat. No. 4,938,949.

The agents of the present invention are preferably formulated in pharmaceutical compositions and then, in accordance with the methods of the invention, administered to a subject, such as a human patient, in a variety of forms adapted to the chosen route of administration. The formulations include, but are not limited to, those suitable for oral, rectal, vaginal, topical, nasal, ophthalmic, or parental (including subcutaneous, intramuscular, intraperitoneal, intratumoral, and intravenous) administration.

Formulations of the present invention suitable for oral administration may be presented as discrete units such as tablets, troches, capsules, lozenges, wafers, or cachets, each containing a predetermined amount of the active agent as a powder or granules, as liposomes containing the vitamin E succinate derivatives, or as a solution or suspension in an aqueous liquor or non-aqueous liquid such as a syrup, an elixir, an emulsion, or a draught. Such compositions and preparations typically contain at least about 0.1 wt-% of the active agent. The amount of vitamin E succinate derivative (i.e., the active agent) is such that the dosage level will be effective to produce the desired result in the subject.

Nasal spray formulations include purified aqueous solutions of the active agent with preservative agents and isotonic agents. Such formulations are preferably adjusted to a pH and isotonic state compatible with the nasal mucous membranes. Formulations for rectal or vaginal administration may be presented as a suppository with a suitable carrier such as cocoa butter, or hydrogenated fats or hydrogenated fatty carboxylic acids. Ophthalmic formulations are prepared by a similar method to the nasal spray, except that the pH and isotonic factors are preferably adjusted to match that of the eye. Topical formulations include the active agent dissolved or suspended in one or more media such as mineral oil, petroleum, polyhydroxy alcohols, or other bases used for topical pharmaceutical formulations.

The tablets, troches, pills, capsules, and the like may also contain one or more of the following: a binder such as gum tragacanth, acacia, corn starch or gelatin; an excipient such as dicalcium phosphate; a disintegrating agent such as corn starch, potato starch, alginic acid, and the like; a lubricant such as magnesium stearate; a sweetening agent such as sucrose, fructose, lactose, or aspartame; and a natural or artificial flavoring agent. When the unit dosage form is a capsule, it may further contain a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, sugar, and the like. A syrup or elixir may contain one or more of a sweetening agent, a preservative such as methyl- or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The active agent may be incorporated into sustained-release preparations and devices.

Preparation of the Compounds

Vitamin E succinate derivatives of the invention may be synthesized by synthetic routes that include processes similar to those well known in the chemical arts, particularly in light of the description contained herein. The starting materials are generally available from commercial sources such as Aldrich Chemicals (Milwaukee, Wis., USA) or are readily prepared using methods well known to those skilled in the art (e.g., prepared by methods generally described in Louis F. Fieser and Mary Fieser, *Reagents for Organic Synthesis*, v. 1-19, Wiley, New York, (1967-1999 ed.); Alan R. Katritsky, Otto Meth-Cohn, Charles W. Rees, *Comprehensive Organic Functional Group Transformations*, v 1-6, Pergamon Press, Oxford, England, (1995); Barry M. Trost and Ian Fleming, *Comprehensive Organic Synthesis*, v. 1-8, Pergamon Press, Oxford, England, (1991); or *Beilsteins Handbuch der organischen Chemie*, 4, Aufl. Ed. Springer-Verlag, Berlin, Germany, including supplements (also available via the Beilstein online database)).

Those skilled in the art will appreciate that other synthetic routes may be used to synthesize the compounds of the invention. Although specific starting materials and reagents are depicted in the reaction schemes and discussed below, other starting materials and reagents can be easily substituted to provide a variety of derivatives and/or reaction conditions. In addition, many of the compounds prepared by the methods described below can be further modified in light of this disclosure using conventional methods well known to those skilled in the art.

The present invention is illustrated by the following examples. It is to be understood that the particular examples, materials, amounts, and procedures are to be interpreted broadly in accordance with the scope and spirit of the invention as set forth herein.

EXAMPLES

Example 1

α-Tocopheryl Succinate as a Scaffold to Develop Potent Inhibitors of Breast Cancer Cell Adhesion The inventors believed that the aliphatic side chain and the semisuccinate might play a crucial role in mediating Vitamin E Succinate's (VES's) anti-adhesion activity. To assess the involvement of the phytyl side chain, the chain length was curtailed by the incremental removal of isopranyl units from the hydrophobic terminus, yielding TS-1 and TS-2, as shown in FIG. 1.

These truncated derivatives showed substantially improved potency vis-à-vis VES in inhibiting the adhesion of 4T1 metastatic breast cancer cells to Matrigel-coated surface, with the relative potency of TS-1>TS-2>VES. Moreover, increasing the rigidity of the side chain by introducing a double bond into TS-1, resulting in compound 1, gave rise to a multifold improvement in the anti-adhesion potency. These findings underscore the role of the phytyl side chain in mediating the anti-adhesion activity.

Further modifications of TS-1 and compound 1 were carried out by replacing the hemisuccinate with ether-linked $C_2$-$C_4$ carboxylic acids to generate two series of compounds (4-6 and 7-9, respectively), for which the rationale was twofold. First, like the phytyl side chain, the carboxylic function is also critically involved in ligand recognition by the target protein. Second, as the hemisuccinate is susceptible to enzymatic digestion, appendage of the carboxylic function through an ether linkage would increase the in vivo metabolic stability of the resulting derivatives. Of all these derivatives, VES was derived from (R,R,R)-α-tocopherol, while the others were synthesized from the chiral precursor (S)-6-hydroxy-2,5,7,8-tetramethyl-chroman-2-carboxylic acid methyl ester according to a general procedure shown in FIG. 1B. However, all side chains used were racemic unless otherwise mentioned.

Results

Figure 2:
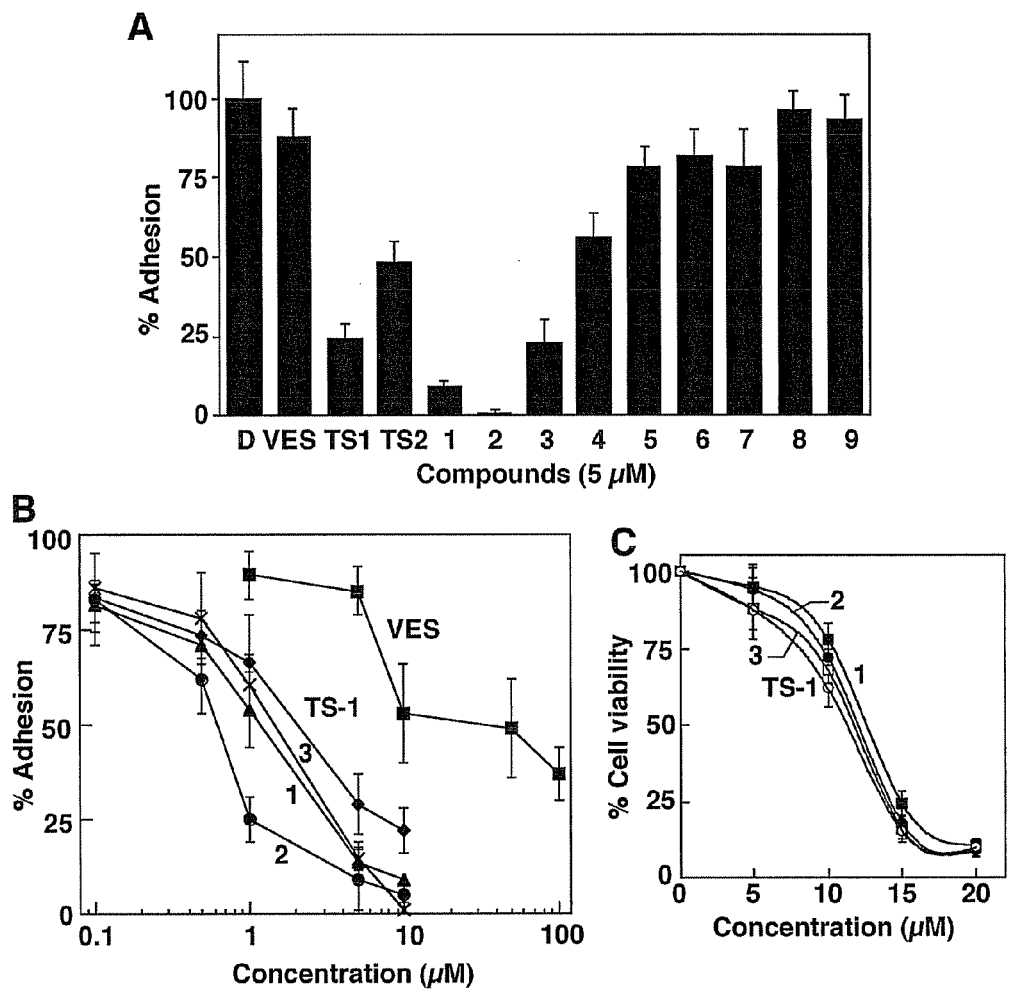
FIG. 2 shows the suppression of 4T1 cell adhesion by VES derivatives. Section (A) shows the effect of VES and various VES derivatives, each at 5 μM, on the adhesion of 4T1 cells to a Matrigel-coated surface. Columns, mean; bars, SD (n=3). Section (B) shows the dose-dependent effect of VES, TS1, and compounds 1-3 on suppressing 4T1 cell adhesion. Points, mean; bars, SD (n=3). Section (C) shows the dose-dependent inhibitory effects of TS-1 and compounds 1-3 on the viability of 4T1 cells. 4T1 cells were treated with individual agents in 2% FBS-supplemented RPMI 1640 medium for 24 h, and cell viability after drug treatment was determined by the MTT assay. Points, mean; bars, SD (n=6).

Pharmacological exploitation of VES to develop potent small-molecule inhibitors of cell adhesion. In this study, the 4T1 mouse mammary tumor cell line was used to investigate the anti-adhesion activity of VES and its derivatives because of the high propensity of 4T1 cells to metastasize to lung, liver, bone and other sites (Tao, et al., BMC Cancer 8, 228 (2008), a characteristic shared by stage 1V human breast tumor cells. As shown, VES exhibited a modest inhibitory effect on 4T1 cell adhesion to a Matrigel-coated surface, as shown in FIG. 2B. While VES inhibited 50% cell adhesion at 10 its activity leveled off between 10 and 50 µM. Conceivably, this weak potency in conjunction with metabolic instability prohibited the clinical use of VES in cancer therapy.

Although the molecular target by which VES inhibited cell adhesion remains undefined, the inventors hypothesized that the phytyl side chain and the succinate moiety were amenable to modifications to improve the anti-adhesion potency of VES. This premise was corroborated by the significantly improved potencies of TS-1 and, to a lesser extent, TS-2, of which the alkyl side chains were shortened by one and two isopranyl units, respectively, as shown in FIG. 2A.

The subsequent lead optimization of TS-1 was performed via two strategies: 1) inserting a double bond α-to the chromane ring to increase the rigidity of the side chain, and 2) replacing the hemisuccinate moiety with alkoxycarboxylic functions with varying chain lengths to increase metabolic stability. These modifications led to two series of derivatives, i.e., series I: compounds 1, 2, and 4-6; series II: compounds 3, and 7-9. Many of these derivatives showed significantly improved activities relative to VES in inhibiting T41 cell adhesion (P<0.05), as shown in FIG. 2A. Of them, compound 2 exhibited the highest potency, followed by compound 1, with the respective $IC_{50}$ values of 0.6 µM, and 1.3 µM vis-à-vis 2.5 µM for TS-1, as shown in FIG. 2B. Compound 2, as distinguished by the α,β-unsaturated, truncated side chain and the ether-linked acetic acid, was three times more potent than its saturated counterpart, compound 3 ($IC_{50}$, 2 µM), underscoring the importance of the rigidity of the alkyl chain in interacting with the target protein(s). Moreover, increases in the length of the alkoxy linker of 2 reduced the anti-adhesion potency. Together, this finding indicates a subtle structure-activity relationship (SAR) in the effect of these VES derivatives on tumor cell adhesion.

Furthermore, evidence was obtained that the ability of VES derivatives to block adhesion was not attributable to drug-induced cell death. Despite high potency in inhibiting cell adhesion, these optimal VES derivatives exhibited modest activities in suppressing 4T1 cell viability in 2% FBS, with $IC_{50}$ values of greater than 10 µM, as shown in FIG. 2C.

Figure 3:
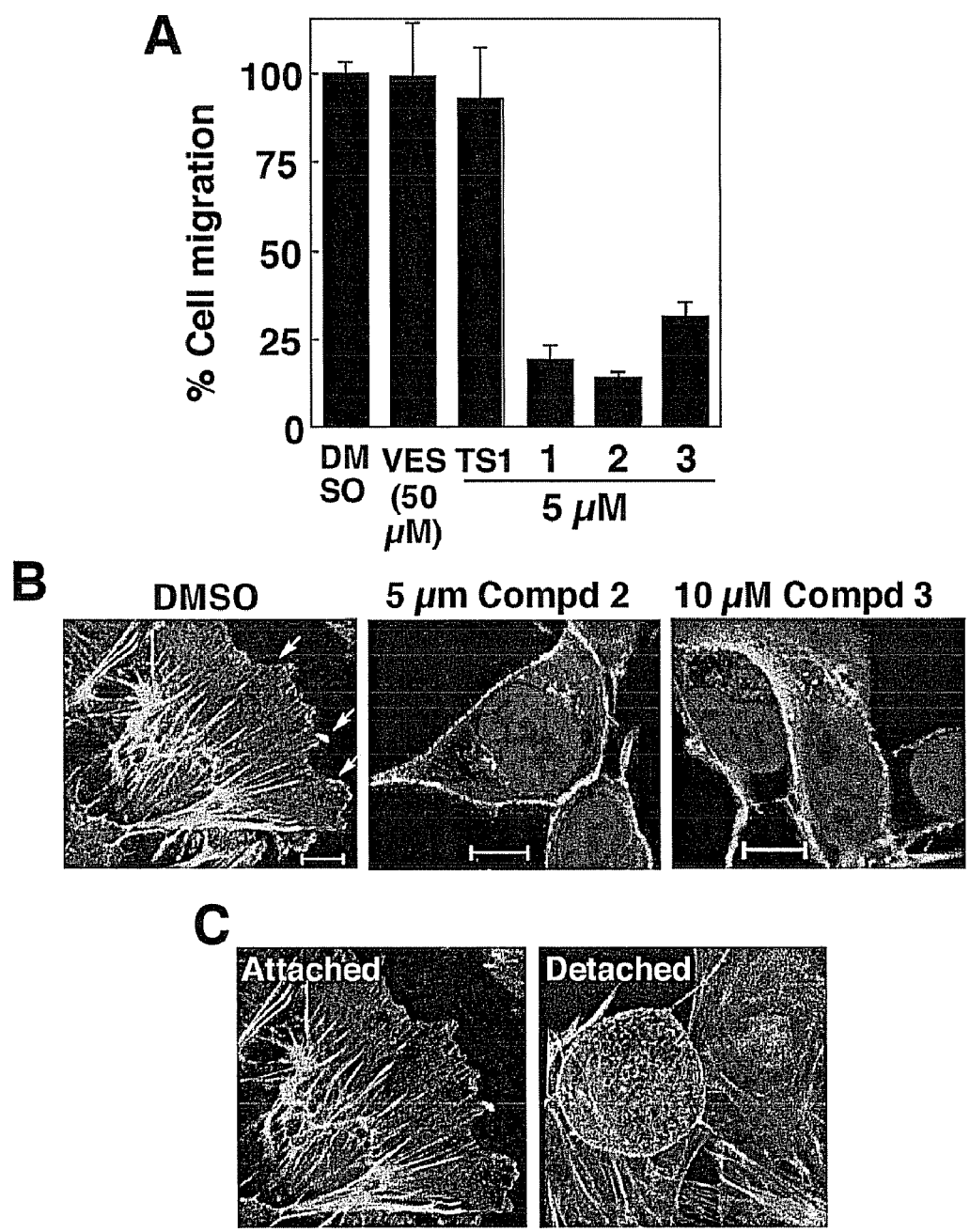
FIG. 3 shows that VES derivatives disrupt the migration and actin cytoskeletal structure of 4T1 cells. Section (A) shows the effects of VES at 50 μM versus TS-1 and compounds 1-3, each at 5 μM, on 4T1 cell migration. Cell motility was analyzed by the Transwell migration assay as described in the Experimental Section. Columns, mean; bars, SD (n=3). Section (B) shows immunocytochemical analysis of the effect of compounds 2 and 3 on lamellipodia formation and actin stress fibers in 4T1 cells after 4 h of treatment. The arrows indicate lamellipodia formation. Section (C) shows the stacked 3-D analysis of the disruption of actin cytoskeletal structure by 5 μM compound 2. The images show that cells with loss of stress fibers were rounded and detached from the surface (right panel), whereas actin filaments in the control cells (left panel) were intact and extended to the edge of the cell body, and the cells were adhered to the surface.

Inhibition of migration and lamellipodia formation of 4T1 metastatic breast tumor cells by VES derivatives. Pursuant to the above finding, the ability of the optimal VES derivatives (compounds 1-3 and TS-1) vis-à-vis VES to inhibit serum-induced 4T1 cell migration was investigated using the Boyden chamber assay. As shown in FIG. 3A, compounds 1-3 at 5 µM were effective in inhibiting cell migration in the order of 2>1>3, in line with that of anti-adhesion. In contrast, TS-1 at 5 µM and VES even at 50 µM showed little effect.

To shed light onto the cellular basis for VES derivative-mediated inhibition of tumor cell migration, the effect of compounds 2 (5 µM) and 3 (10 µM) on the actin cytoskeleton in 4T1 cells were investigated by immunocytochemistry. After 4 hours of exposure, these agents caused rapid dissolution of stress fiber and impairment of lamellipodia formation at the leading edge of 4T1 cells (FIG. 3B). Quantitative analysis indicates that treatment of 4T1 cells with compounds 2 (5 µM) and 3 (10 µM) led to a reduction in the fluorescent intensity of F-actin by 84% and 70%, respectively, relative to the DMSO control (P<0.001). Furthermore, the 3-D imaging of drug-treated cells showed detachment from neighboring cells or the surface of the culture dish as a result of stress fiber loss, as shown in FIG. 3C. Moreover, it was observed that treatment of 4T1 cells with compound 2 or 3 gave rise to the accumulation of small vesicles in areas surrounding the nucleus where the endoplasmic reticulum is typically located. The disintegration of the endoplasmic reticulum membrane might be associated with the drug-mediated loss of actin stress fibers.

Figure 4:
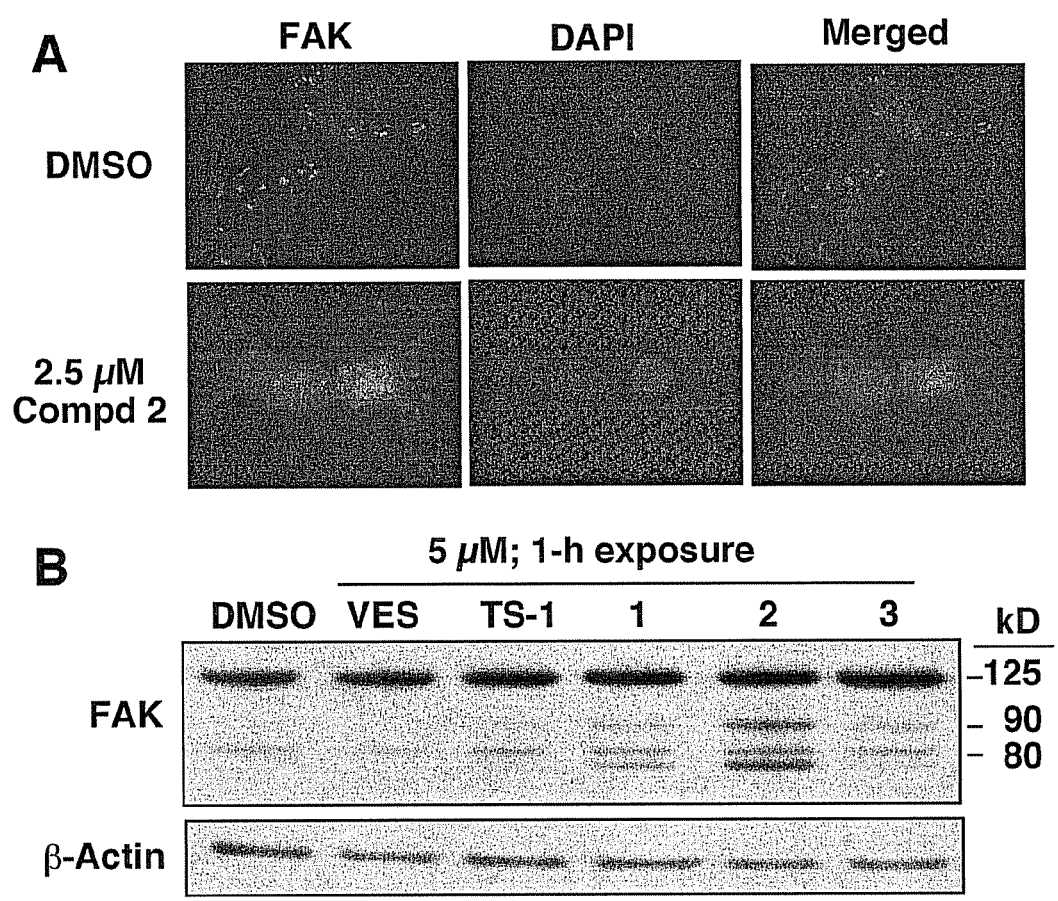
FIG. 4 shows the effects of VES versus TS-1 and compounds 1-3 on the expression of focal adhesion kinase (FAK), a central component of cell adhesion. Section (A) shows 4T1 cells that were treated with individual agents at the indicated concentration for 1 h, and cell lysates were immunoblotted with anti-FAK monoclonal antibody. Section (B) shows 4T1 cells that were treated with 2.5 μM compound 2 or DMSO for 1 h, fixed, and immunostained with anti-FAK antibody. The distinct punctate staining pattern of FAK representing adhesive contacts at the cell periphery was evident in vehicle-treated 4T1 cells, but was no longer detectable following treatment with compound 2.

VES derivatives target focal adhesion kinase (FAK) degradation. Considering the important role of FAK in regulating the formation of focal adhesions and actin stress fibers (McLean et al., Nat Rev Cancer 5, 505-15 (2005)), the effect of compound 2 on focal adhesion sites in 4T1 cells was assessed by immunostaining with anti-FAK antibodies, the results of which are shown in FIG. 4A. While FAK staining displayed a typical punctate pattern representing the focal adhesion sites in the DMSO-treated control cells, compound 2 treatment led to loss of focal adhesion sites, paralleling that of the aformentioned stress fiber dissolution, shown in FIG. 3B. It is noteworthy that the disruption of actin stress fibers and focal adhesion by compound 2 is reminiscent of that induced by mannitol in neuroblastoma cells. Kim et al. J Biol Chem 277, 27393-400 (2002). As mannitol-induced cytoskeletal changes were preceded by the degradation of FAK, the effects of compound 2 relative to VES, TS-1, and compounds 1 and 3, each at 5 µM, on FAK protein stability in 4T1 cells was investigated by Western blotting. As shown in FIG. 4B, treatment with compound 2, and to a lesser extent, 1 and 3, induced FAK degradation, resulting in two major cleavage fragments with molecular masses of approximately 90 and 80 kDa. This degradation, however, was less evident or not appreciable in cells treated with TS-1 and VES, which paralleled the respective activities in blocking 4T1 cell adhesion.

Discussion

Cell adhesion has emerged as a promising therapeutic target in light of its critical role in promoting the invasive phenotype of cancer cells. Schmidmaier et al., Curr Med Chem 15, 978-90 (2008). Accordingly, this study focused on the pharmacological exploitation of VES to develop potent anti-adhesion agents. SAR analysis indicates that there exists a high degree of structural cooperativity between the phytyl side chain and the alkoxycarboxylic terminus of VES in determining its anti-adhesion activity. Among various VES derivatives examined, compound 2 provided an-order-of-magnitude higher potency relative to VES in blocking 4T1 cell adhesion ($IC_{50}$, 0.6 µM versus 10 µM) and migration. Moreover, this high anti-adhesion potency was independent of compound 2's cytotoxicity in 4T1 cells. The dissociation of these two pharmacological activities suggests a unique mode of mechanism underlying the strong activity of compound 2 in inhibiting cell adhesion. Evidence was obtained that the ability of compound 2 to block cell adhesion and migration was attributable to its effect on disrupting the formation of focal adhesion and actin cytoskeletal structures including lamellipodia and stress fibers through the stimulation of FAK degradation. This mode of action is reminiscent of that of mannitol-induced disruption of cytoskeletal structures, however, without the concurrent induction of apoptosis. Thus, the mechanism by which compound 2 induces FAK degradation warrants further investigation given the importance of FAK signaling in mediating tumor angiogensis and metastasis. Mitra et al., Curr Opin Cell Biol 18, 516-23 (2006). From a mechanistic perspective, compound 2 differs from other agents that target FAK proteolysis or FAK kinase activity. Ochel et al., Mol Genet Metab 66, 24-30 (1999) and Roberts et al., Cancer Res 68, 1935-44 (2008). It might therefore provide a useful pharmacological probe to shed light onto the cellular regulation of FAK signaling and its role in facilitating tumor progression.

CONCLUSION

Cell adhesion represents an important therapeutic target not only in oncology but also in acute and chronic inflammatory diseases such as inflammatory bowel diseases and autoimmune inflammation. To date, most of the therapeutic development in targeting cell adhesion has focused on the blockade of integrin-ligand interactions by using monoclonal antibodies, antisense oligonucleotides, or small interference (si)RNAs, while very few small-molecule agents have been developed. Consequently, the high potency and unique mechanism of vitamin E succinate derivatives such as compound 2 in inhibiting cell adhesion through FAK degradation might have therapeutic relevance to the treatment of cancer, and metastatic cancer in particular. The underlying mechanism and in vivo testing of compound 2 to suppress 4T1 cell metastasis are currently underway.

Experimental Section

Chemical reagents and organic solvents were purchased from Sigma-Aldrich (St. Louis, Mo.) unless otherwise mentioned. Nuclear magnetic resonance spectra ($^1$H NMR) were measured on a Bruker DPX 300 model spectrometer. Chemical shifts (δ) were reported in parts per million (ppm) relative to the TMS peak. Electrospray ionization mass spectrometry analyses were performed with a Micromass Q-T of II high-resolution electrospray mass spectrometer. The purity of all tested compounds are higher than 95% by elemental analyses, which were performed by Atlantic Microlab, Inc. (Norcross, Ga.), and were reported to be within 0.4% of calculated values. Flash column chromatography was performed using silica gel (230-400 mesh). Synthesis of VES, TS-1, and TS-2 was carried out as previously described (Shiau et al., J Biol Chem 281, 11819-25 (2006), and the two series of compounds: 1, 2, 4-6, and 3, 7-9, were synthesized according to the general scheme described in FIG. 1B, which illustrates the synthesis of compound 1 as an example.

Succinic acid mono-[2-(4,8-dimethyl-non-1-enyl)-2,5,7,8-tetramethyl-chroman-6-yl]ester (1). Step a. A solution of 6-hydroxy-2,5,7,8-tetramethyl-chroman-2-carboxylic acid methyl ester (i, 41.9 mmol), t-butyl-dimethyl-silyloxy chloride (62.8 mmol), and imidazole (172.2 mmol) in 100 mL of DMF was stirred at 85-95° C. for 16 h, and cooled to room temperature. The solution was diluted with 200 mL of ethyl acetate, washed, in tandem, with H$_2$O, 1% HCl, saturated NaHCO$_3$, and brine, dried with Na$_2$SO$_4$, and concentrated. Purification by flash silica gel chromatography gave the product, 6-(t-butyl-dimethyl-silyloxy)-2,5,7,8-tetramethyl-chroman-2-carboxylic acid methyl ester (ii), as white solid in 99% yield. $^1$H NMR (300 MHz, CDCl$_3$) δ 0.11 (s, 6H), 1.04 (s, 9H), 1.62 (s, 3H), 1.86-1.76 (m, 1H), 2.01 (s, 3H), 2.11 (s, 3H), 2.16 (s, 3H), 2.22-2.30 (m, 1H), 3.49-3.65 (m, 2H), 3.69 (s, 3H), 4.22 (s, 1H).

Step b. To a stirring solution of compound ii (15 g, 39.7 mmol) in 150 mL of dry hexane at −60° C. was added 40 mL of 1 M di-isobutyl aluminum hydride (DIBAL-H) in hexane dropwise over a period of 90 min. The solution was stirred in ice bath for 1 h, and 100 mL of methanol followed by 75 mL of H$_2$O was added to the solution to quench the reaction. The mixture was extracted with 90 mL of ethyl acetate/hexane (1:2) three times, and the pooled organic phase was dried and concentrated. The residue was purified by chromatography, resulting in 6-(t-butyl-dimethyl-silyloxy)-2,5,7,8-tetramethyl-chroman-2-carbaldehyde (iii) as white solid in 88% yield. $^1$H NMR (300 MHz, CDCl$_3$) δ 0.11 (s, 6H), 1.04 (s, 9H), 1.39 (s, 3H), 1.76-1.86 (m, 1H), 2.01 (s, 3H), 2.11 (s, 3H), 2.16 (s, 3H), 2.22-2.30 (m, 1H), 3.49-3.65 (m, 2H), 9.62 (s, 1H).

Step c. To a suspension of 1-bromo-3,7-dimethyl octanyl phosphonium (1.05 mmol) in 20 mL of anhydrous THF at 0° C. was added 1.05 mL of 1 M lithium bis(trimethysilyl)amide in THF. The mixture was stirred at 0° C. for 30 min, and compound iii (1 mmol) in 10 mL of THF was slowly added over a period of 1 h. After being stirred at room temperature for 1 h, the solution was concentrated, diluted with 20 mL of ethyl acetate, and washed, in tandem, with H$_2$O and brine. The residue was purified by flash silica gel chromatography to afford t-butyl-[2-(4,8-dimethyl-non-1-enyl)-2,5,7,8-tetramethyl-chroman-6-yloxy]-dimethylsilane (iv) as colorless oil in 80% yield. $^1$H NMR (300 MHz, CDCl$_3$) δ 0.11 (s, 6H), 0.86-0.95 (m, 6H), 1.04 (s, 9H), 1.39 (s, 1H), 1.49-1.56 (m, 1H), 1.76-1.86 (m, 1H), 2.01-2.06 (m, 2H), 2.11 (s, 3H), 2.17 (s, 6H), 2.25-2.32 (m, 1H), 2.62 (t, J=6.60 Hz, 2H), 5.30-5.44 (m, 2H).

Step d. A solution of compound 1v (0.67 mmol) in anhydrous THF (10 mL) was cooled to 0° C., to which was added 0.3 mL of 1 M TBAF (tetrabutyl ammonium fluoride) in THF. After being stirred at 0° C. for 1 h, the solution was concentrated, diluted with ethyl acetate (20 mL), washed with water and brine, and dried. Purification of the residue by flash silica gel chromatography gave 2-(4,8-Dimethyl-non-1-enyl)-2,5,7,8-tetramethyl-chroman-6-ol (v) as colorless syrup in 96% yield. $^1$H NMR (300 MHz, CDCl$_3$) δ): 0.86-0.95 (m, 9H), 1.39 (s, 1H), 0.98-1.56 (m, 11H), 1.76-1.86 (m, 1H), 2.01-232 (m, 12H), 2.62 (t, J=6.60 Hz, 2H), 4.20 (s, 1H), 5.31-5.42 (m, 2H).

Step e. A mixture of compound v (0.58 mmol), succinic anhydride (1.16 mmol) and pyridine (93 μL) in dry CH$_2$Cl$_2$ (15 mL) was stirred at refluxing temperature for 16 h. The solution was cooled to room temperature, concentrated, and purified by flash silica gel chromatography to give compound 1 as white solid in 88% yield. $^1$H NMR (300 MHz, CDCl$_3$) 0.75-0.90 (m, 9H), 1.00-1.58 (m, 12H), 1.68-1.82 (m, 2H), 1.96 (s, 3H), 2.01 (s, 3H), 2.06-2.28 (m, 4H), 2.30-2.40 (m, 1H), 2.58 (t, J=5.94 Hz, 2H), 2.83 (t, J=6.42 Hz, 2H), 2.94 (t, J=5.49 Hz, 2H), 5.31-5.38 (m, 2H); HRMS exact mass of C$_{28}$H$_{42}$O$_5$ (M+Na)$^+$, 481.2930 amu; observed mass of (M+Na)+, 481.2947 amu. Anal. Calcd. (C, 73.33, H, 9.23, O, 17.44) Found, (C, 73.49, H, 9.46, O, 17.56.

General Procedure for Preparing Ether-Linked Alkanoic Acid Derivatives of Compound v (Step f). A mixture of compound v (0.58 mmol) and NaH (0.64 mmol) in anhydrous DMF (5 mL) was stirred at 0° C. for 30 min, to which bromoalkanoic acid methyl ester (1.16 mmol) in DMF (1 mL) was added. After being stirred at room temperature for 16 h, the reaction mixture was diluted with ethyl acetate, washed with water and brine, dried, and concentrated. The crude residue was treated with 1 N NaOH in methanol for 3 h. The solution was neutralized with 1N HCl aqueous solution, concentrated, diluted with ethyl acetate, washed with water and brine, dried, and concentrated. Purification of the residue by flash column chromatography gave compounds 2, and 4-6 as white solid in 70%-78% yield.

[2-(4,8-Dimethyl-non-1-enyl)-2,5,7,8-tetramethyl-chroman-6-yloxy]-acetic acid (2). $^1$H NMR (300 MHz, CDCl$_3$) δ 0.64-0.87 (m, 9H), 0.94-1.56 (m, 11H), 1.70-1.83 (m, 1H), 1.89-2.06 (m, 2H), 2.10-2.34 (m, 10H), 2.48-2.63 (m, 2H), 4.35 (s, 2H), 5.41 (d, J=18.75 Hz, 2H). 4.35 (s, 2H), 2.63-2.48 (m, 2H), 2.34-2.10 (m, 10H), 2.06-1.89 (m, 2H), 1.83-1.70 (m, 1H), 1.56-0.94 (m, 11H), 0.87-0.64 (m, 9H); HRMS exact mass of C$_{26}$H$_{40}$O$_4$ (M+Na)$^+$, 439.2824 amu; observed mass of (M+Na)$^+$, 439.2840 amu. Anal. Calcd. (C, 74.96, H, 9.68, O, 15.36); Found, C, 75.13, H, 9.77, O, 15.47.

3-[2-(4,8-Dimethyl-non-1-enyl)-2,5,7,8-tetramethyl-chroman-6-yloxy]-propionic acid (4). $^1$H NMR (300 MHz, CDCl$_3$) δ 0.65-0.85 (m, 9H), 1.04-1.56 (m, 12 h), 1.74-1.81 (m, 1H), 1.90-2.41 (m, 13H), 2.54 (t, J=6.75 Hz), 2.80 (t, J=6.36 Hz, 2H), 3.99 (t, J=6.3 Hz, 2H), 5.40 (d, J=18.75 Hz, 2H); HRMS exact mass of C$_{27}$H$_{42}$O$_4$ (M Na)$^+$, 453.2981 amu; observed mass of (M+Na)$^+$, 453.3013 amu. Anal. Calcd. (C, 75.31, H, 9.83, O, 14.86); Found, C, 75.23, H, 9.87, O, 14.67.

4-[2-(4,8-Dimethyl-non-1-enyl)-2,5,7,8-tetramethyl-chroman-6-yloxy]-butyric acid (5). $^1$H NMR (300 MHz, CDCl$_3$) δ 0.68-0.90 (m, 9H), 1.04-1.56 (m, 17H), 1.74-1.81 (m, 1H), 1.90-2.07 (m, 2H), 2.09-2.40 (m, 12H), 2.58 (t, J=5.88 Hz, 2H), 2.69 (t, J=7.40 Hz, 2H), 3.70 (t, J=6.0 Hz, 2H), 5.37-5.44 (m, 2H); HRMS exact mass of C$_{28}$H$_{44}$O$_4$ (M+Na)$^+$, 467.3138 amu; observed mass of (M+Na)$^+$, 467.3161 amu. Anal. Calcd. (C, 75.63, H, 9.97, O, 14.39); Found, C, 75.58, H, 9.89, O, 14.33.

5-[2-(4,8-Dimethyl-non-1-enyl)-2,5,7,8-tetramethyl-chroman-6-yloxy]-pentanoic acid (6). $^1$H NMR (300 MHz, CDCl$_3$) δ 0.69-0.89 (m, 9H), 0.99-1.57 (m, 14H), 1.74-2.05 (m, 6H), 2.09 (s, 3H), 2.13 (s, 3H), 2.17 (s, 3H), 2.24-2.40 (m, 1H), 2.48 (t, J=6.69 Hz, 2H), 2.57 (t, J=5.91 Hz, 2H), 3.66 (t, J=5.76 Hz, 2H), 5.36-5.43 (m, 2H); HRMS exact mass of C$_{29}$H$_{46}$O$_4$ Na)$^+$, 481.3294 amu; observed mass of (M+Na)$^+$, 481.3314 amu. Anal. Calcd. (C, 75.94, H, 10.11, O, 13.95); Found, C, 75.83, H, 10.06, O, 13.92.

General Procedure for Hydrogenolysis (step g). A mixture of the α,β-unsaturated acid (compounds 2 and 4-6; 0.37 mmol), 10% Pd/C (20 mg) in ethyl acetate was shaken under H$_2$ at 56 psi for 16 hrs, filtered, and concentrated. Purification of the residue by flash silica gel column gave compounds 3 and 7-9 as white solid in quantitative yield.

[2-(4,8-Dimethyl-nonyl)-2,5,7,8-tetramethyl-chroman-6-yloxy]-acetic acid (3). $^1$H NMR (300 MHz, CDCl$_3$) δ 0.86 (dd, J=6.57, 6.09 Hz, 9H), 1.03-1.61 (m, 19H), 1.74-1.86 (m, 2H), 2.09 (s, 3H), 2.14 (s, 3H), 2.18 (s, 3H), 2.58 (t, J=6.69 Hz, 2H), 4.36 (s, 2H); HRMS exact mass of C$_{26}$H$_{42}$O$_4$ (M Na)$^+$, 441.2981 amu; observed mass of C$_{26}$H$_{42}$O$_4$ (M Na)$^+$, 441.3000 amu. Anal. Calcd. (C, 74.60, H, 10.11, O, 15.29); Found, C, 74.46, H, 10.31, O, 15.40.

3-[2-(4,8-Dimethyl-nonyl)-2,5,7,8-tetramethyl-chroman-6-yloxy]-propionic acid (7). $^1$H NMR (300 MHz, CDCl$_3$) δ 0.83 (dd, J=5.22, 5.09 Hz, 9H), 0.99-1.56 (m, 18H), 1.69-1.81 (m, 2H), 2.05 (s, 3H), 2.10 (s, 3H), 2.14 (s, 3H), 2.53 (t, J=6.75 Hz; 2H), 2.80 (t, J=6.36 Hz, 2H), 3.92 (t, J=6.33 Hz, 2H); HRMS exact mass of C$_{27}$H$_{44}$O$_4$ (M+Na)$^+$, 455.3138 amu; observed mass of C$_{27}$H$_{44}$O$_4$ (M+Na)$^+$, 455.3152 amu. Anal. Calcd. (C, 74.96, H, 10.25, O, 14.79); Found C, 74.83, H, 10.19, O, 14.67.

4-[2-(4,8-Dimethyl-nonyl)-2,5,7,8-tetramethyl-chroman-6-yloxy]-butyric acid (8). $^1$H NMR (300 MHz, CDCl$_3$) δ 0.86 (dd, J=5.01, 5.84 Hz, 9H), 1.03-1.63 (m, 18H), 1.71-1.88 (m, 2H), 2.09-2.17 (m, 11H), 2.58 (t, J=6.49 Hz, 2H), 2.68 (t, J=7.42 Hz, 2H), 3.70 (t, J=5.98 Hz, 2H); HRMS exact mass of C$_{28}$H$_{46}$O$_4$ (M+Na)$^+$, 469.3294 amu; observed mass of C$_{28}$H$_{46}$O$_4$+Na)$^+$, 469.3321 amu. Anal. Calcd. (C, 75.29, H, 10.38, O, 14.33); Found C, 75.35, H, 10.30, O, 14.46.

5-[2-(4,8-Dimethyl-nonyl)-2,5,7,8-tetramethyl-chroman-6-yloxy]-pentanoic acid (9). $^1$H NMR (300 MHz, CDCl$_3$) δ 0.86 (dd, J=5.13, 5.96 Hz, 9H), 1.05-1.62 (m, 18H), 1.70-1.88 (m, 6H), 2.09 (s, 3H), 2.13 (s, 3H), 2.17 (s, 3H), 2.48 (t, J=7.05 Hz, 2H), 2.57 (t, J=6.81 Hz, 2H), 3.66 (t, J=5.92 Hz, 2H); HRMS exact mass of C$_{29}$H$_{48}$O$_4$ (M Na)$^+$, 483.3451 amu; observed mass of C$_{29}$H$_{48}$O$_4$ (M+Na)$^+$, 483.3472 amu. Anal. Calcd. (C, 75.61, H, 10.50, O, 13.89); Found C, 75.75, H, 10.66, O, 13.91.

Cells and Cell Culture. 4T1 metastatic breast cancer cells were purchased from American Type Culture Collection (Manassas, Va.). Cells were cultured at 37° C. in 5% CO$_2$ in RPMI 1640 medium supplemented with penicillin-streptomycin and 10% fetal bovine serum (Invitrogen, Carlsbad, Calif.).

Adhesion Assay. Ninety six-well plates were coated with 12% (v/v) Matrigel (BD Biosciences) at 37° C. for 1 hour, washed twice with washing buffer (0.1% BSA-containing RPMI medium) followed by blocking with 0.5% BSA-containing RPMI medium at 37° C. for 60 minutes. 4T1 cells were treated with individual derivatives at the indicated concentrations at 37° C. in a CO$_2$ incubator for 60 minutes, and 2×10$^4$ cells in 100 μl were seeded in each well. Cells were allowed to adhere to the Matrigel-coated surface for 30 min at 37° C., and nonadherent cells were removed by gentle washing with the aforementioned washing buffer. Adherent cells were fixed with 10% formalin, stained with 0.5% crystal violet, and dissolved in 2% SDS. Absorbance at 570 nm was measured in an ELISA plate reader (Molecular device, Sunnyvale, Calif.).

Migration Assay. 4T1 cells were trypsinized for 5 min, washed, and suspended in 0.2% FBS-supplemented RPMI 1640 medium. Five×10$^4$ cells in 0.5 ml of 0.2% FBS-supplemented RPMI medium containing individual test agents at the indicated concentrations were added to the upper chamber (i.e., insert) of each Transwell system (12 mm, polycarbonate, 12-μm pore, Millipore) in a 24-well plate, and incubated at 37° C. in a CO$_2$ incubator for 30 min. The inserts were then switched to a new well containing 10% FBS-supplemented RPMI 1640 medium for 24 h. All cells in each well were fixed with 10% formalin followed by staining with 0.5% crystal violet. To quantify migrated cells, cells attached to the bottom side of the upper chamber and in the bottom of the well were wiped with a moistened cotton swab, which was then rinsed with 80 μl DDW. The cells were then dissolved by the addition of 320 μl 100% methanol. Enumeration of non-migrated cells was done by placing the chamber into 400 μl of 80% methanol, and incubating for 30 min in an orbital shaker. Absorbance at 570 nm was measured in an ELISA plate reader. Percentage of cell migration in each well was calculated using the following equation: % of migration=100×[(O.D. of migrated cells)−(O.D. of background)]/{[(O.D. of migrated cells)−(O.D. of background)]+[(O.D. of non-migrated cells)−(O.D. of background)]}. The migration activity in each treatment group is expressed as a percentage of that in the vehicle controls, which was considered to be 100%.

F-actin Immunostaining To assess the effect of test compounds on actin cytoskeletal structures, cells were seeded onto coverslips in six-well plates and incubated overnight, followed by exposure to individual agents at the indicated concentrations for 4 h in 2% FBS-containing RPMI 1640 medium. Cells were then fixed in 3.7% formaldehyde, permeabilized with PBS containing 0.1% Triton X-100 and 0.1% BSA for 1 h, and then incubated with Alexa Fluor 488 phallotoxin staining solution (Molecular Probes, Inc., Eugene, Oreg.) for 30 min. Nuclear counterstaining was achieved by use of 4,6-diamidino-2-phenylindole (DAPI)-containing mounting medium. Immunocytochemically labeled cells were visualized and images captured using a Zeiss microscope (LSM510) with Argon and HeNe lasers, appropriate filters (excitation wavelengths were 488 nm and 543 nm), and a 63×1.4 numerical aperture water immersion lens. Differences in fluorescence intensity were calculated from comparisons of the control sample with each of the treatment samples under the same threshold using MacBiophotonic ImageJ software (National Institutes of Health) and were expressed as percentages of the fluorescent intensity of the untreated control. Statistical significance was evaluated using Student's t-test and considered significant at $P<0.05$.

Cell Viability Assay. Cell viability was assessed by using the 3-(4,5-dimethylthiazol-2-yl)-2,5-diphenyl-2H-tetrazolium bromide (MTT) assay in six replicates in 96-well plates. The 4T1 cells were seeded at 6000 cells per well in 10% FBS-supplemented RPMI 1640 for 24 h, followed by treatments with various compounds in 2% FBS-supplemented RPMI 1640 at the indicated concentrations. Controls received DMSO at a concentration equal to that in drug-treated cells. After the end of incubation, MTT (0.5 mg/ml) in 10% FBS-supplemented RPMI 1640 was added to each well, and cells were incubated at 37° C. for 2 h. Medium was removed and the reduced MTT dye was solubilized in DMSO (200 μl/well). Absorbance was determined at 570 nm by a 96-well plate reader.

Example 2

Synthesis of Additional Vitamin E Succinate Derivatives

Figure 5:
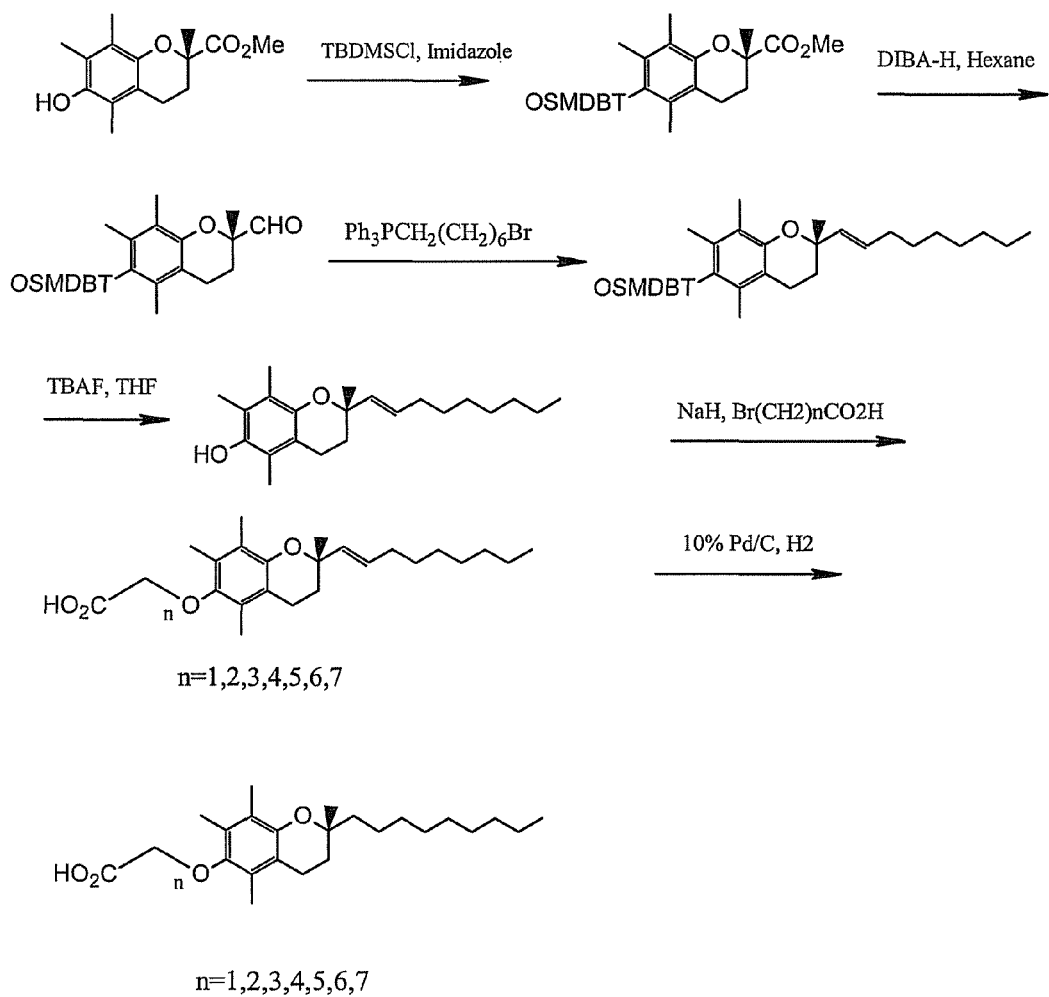
FIG. 5 provides a reaction scheme for the synthesis of vitamin E succinate derivatives including non-1-enyl and nonanyl groups.
Figure 6:
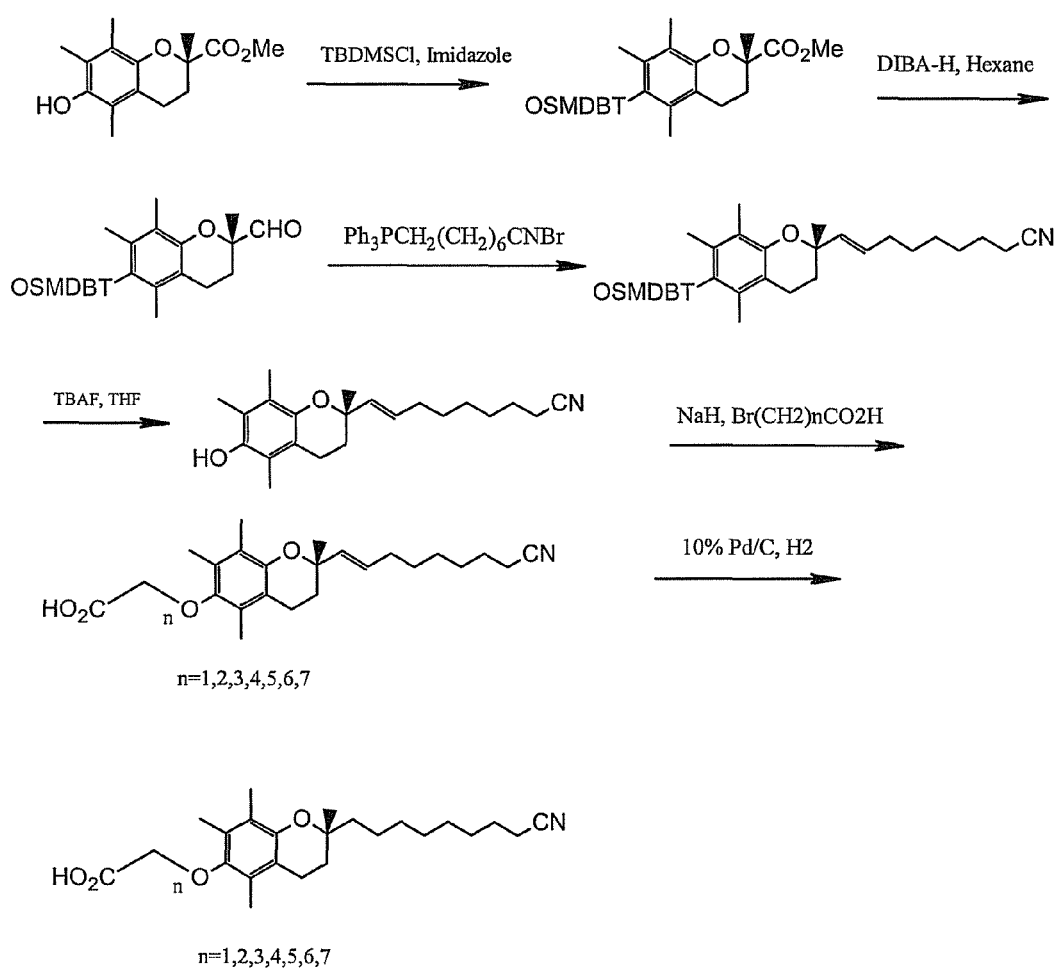
FIG. 6 provides a reaction scheme for the synthesis of vitamin E succinate derivatives including non-8-enylnitrile and nonanylnitrile groups.

Example I describes the preparation of vitamin E succinate derivatives including 4,8-dimethyl-non-1-enyl and 4,8-dimethyl-nonyl groups in the $R^1$ position of formula (I). Vitamin E succinate derivatives including non-1-enyl, nonanyl, non-8-enylnitrile, and nonanylnitrile groups in the $R^1$ position of formula (I) can also be prepared. While the starting compounds used to prepare vitamin E succinate derivatives including non-1-enyl, nonanyl, non-8-enylnitrile, and nonanylnitrile groups differ, the reagents and conditions used will be essentially the same as those described for vitamin E succinate derivatives including 4,8-dimethyl-non-1-enyl and 4,8-dimethyl-nonyl groups. The reaction scheme for vitamin E succinate derivatives including non-1-enyl and nonanyl groups is shown in FIG. 5, whereas the reaction scheme for vitamin E succinate derivatives including non-8-enylnitrile and nonanylnitrile groups is shown in FIG. 6.

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

What is claimed is:

1. A compound according to formula (I):

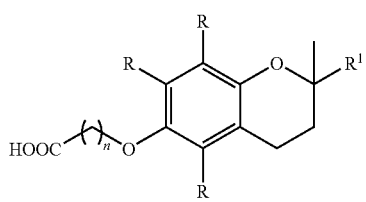

(I)

wherein R is independently selected from hydrogen and methyl; $R^1$ is selected from the group consisting of 4,8-dimethyl-non-1-enyl, non-1-enyl, and non-8-enylnitrile groups; and n is an integer from 1 to 7, or a pharmaceutically acceptable salt thereof.

2. The compound of claim 1, wherein n is 1 or 2.

3. The compound of claim 1, wherein $R^1$ is a 4,8-dimethyl-non-1-enyl group.

4. The compound of claim 1, wherein $R^1$ is a non-1-enyl group.

5. The compound of claim 1, wherein $R^1$ is a non-8-enylnitrile group.

6. A method of treating cancer in a subject, comprising administering a therapeutically effective amount of a pharmaceutical composition including a compound of Formula (I):

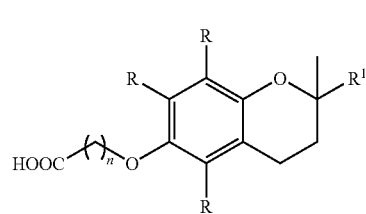

(I)

wherein R is independently selected from hydrogen and methyl; $R^1$ is selected from the group consisting of 4,8-dimethyl-non-1-enyl, non-1-enyl, and non-8-enylnitrile groups; and n is an integer from 1 to 7, or a pharmaceutically acceptable salt thereof.

7. The method of claim 6, wherein the cancer is metastatic cancer.

8. The method of claim 6, wherein $R^1$ is selected from the group consisting of 4,8-dimethyl-non-1-enyl, non-1-enyl, and non-8-enylnitrile.

9. The method of claim 6, wherein n is 1 or 2.

10. The method of claim 6, wherein n is 1 and $R^1$ is 4,8-dimethyl-non-1-enyl.

11. A method of inhibiting cell adhesion in a subject in need thereof by administering a therapeutically effective amount of a pharmaceutical composition including a compound of Formula (I):

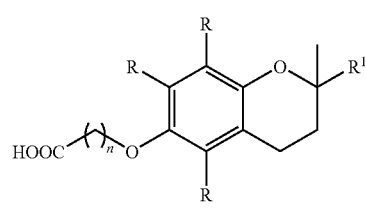

(I)

wherein R is independently selected from hydrogen and methyl; $R^1$ is selected from the group consisting of 4,8-dimethyl-non-1-enyl, non-1-enyl, and non-8-enylnitrile groups; and n is an integer from 1 to 7, or a pharmaceutically acceptable salt thereof.

12. The method of claim 11, wherein n is 1 or 2.

13. The method of claim 11, wherein n is 1 and $R^1$ is 4,8-dimethyl-non-1-enyl.

* * * * *